(12) United States Patent
McIver et al.

(10) Patent No.: US 11,413,151 B1
(45) Date of Patent: Aug. 16, 2022

(54) INTERVERTEBRAL IMPLANT SYSTEM FOR AN INLINE TECHNIQUE WITH PATIENT IN A LATERAL DECUBITUS POSITION

(71) Applicant: GLOBUS MEDICAL, INC., Audubon, PA (US)

(72) Inventors: Irelyn McIver, Philadelphia, PA (US); Mark Miccio, Lynbrook, NY (US); John Bohenick, Troy, MI (US); Jason Zappacosta, Philadelphia, PA (US); Michael Moretti, Pottstown, PA (US); Manuel Seas, McAllen, TX (US); Jason Gray, East Greenville, PA (US); Elizabeth Marks, Collegeville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 17/218,448

(22) Filed: Mar. 31, 2021

(51) Int. Cl.
| | |
|---|---|
| *A61F 2/46* | (2006.01) |
| *A61F 2/30* | (2006.01) |
| *A61F 2/44* | (2006.01) |

(52) U.S. Cl.
CPC .......... *A61F 2/30749* (2013.01); *A61F 2/442* (2013.01); *A61F 2/447* (2013.01); *A61F 2/4611* (2013.01); *A61F 2002/30266* (2013.01); *A61F 2002/30579* (2013.01); *A61F 2002/4615* (2013.01)

(58) Field of Classification Search
CPC .......... A61F 2/44; A61F 2/4455; A61F 2/447; A61F 2002/30889; A61F 2/46; A61F 2/4611
See application file for complete search history.

(56) References Cited

U.S. PATENT DOCUMENTS

| | | | | |
|---|---|---|---|---|
| 11,058,542 | B1 * | 7/2021 | Lee | A61F 2/4603 |
| 2013/0226300 | A1 * | 8/2013 | Chataigner | A61F 2/4455 |
| | | | | 623/17.16 |
| 2016/0058565 | A1 * | 3/2016 | Zappacosta | A61F 2/4611 |
| | | | | 623/17.16 |
| 2016/0242927 | A1 * | 8/2016 | Seifert | A61F 2/4455 |
| 2017/0340453 | A1 * | 11/2017 | Kaufmann | A61F 2/4455 |
| 2018/0042732 | A1 * | 2/2018 | Seifert | A61F 2/4455 |
| 2018/0303623 | A1 * | 10/2018 | Shoshtaev | A61F 2/4455 |
| 2019/0000637 | A1 * | 1/2019 | Gilbride | A61B 17/8685 |

* cited by examiner

*Primary Examiner* — Eduardo C Robert
*Assistant Examiner* — Michelle C Eckman

(57) ABSTRACT

A surgical implant system includes a surgical implant for securing adjacent vertebrae of a spine to each other. The surgical implant includes a spacer having at least one implant eyelet. The surgical implant system also includes at least one vertebral anchor configured for insertion through the at least one implant eyelet to fasten the surgical implant to the spine. The vertebral anchor has a tip portion, a head portion, an elongate shank extending from the head portion, and an elongate fin extending from the head portion and along a surface of the elongate shank. The elongate shank and the elongate fin form a generally t-shaped cross-section.

19 Claims, 38 Drawing Sheets

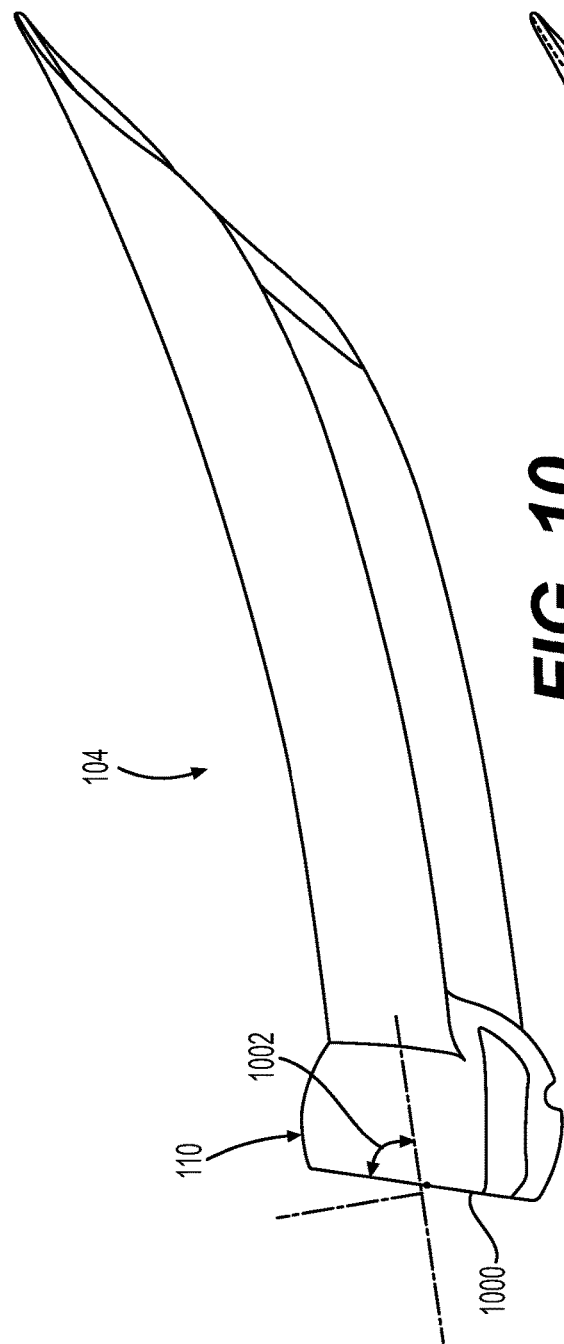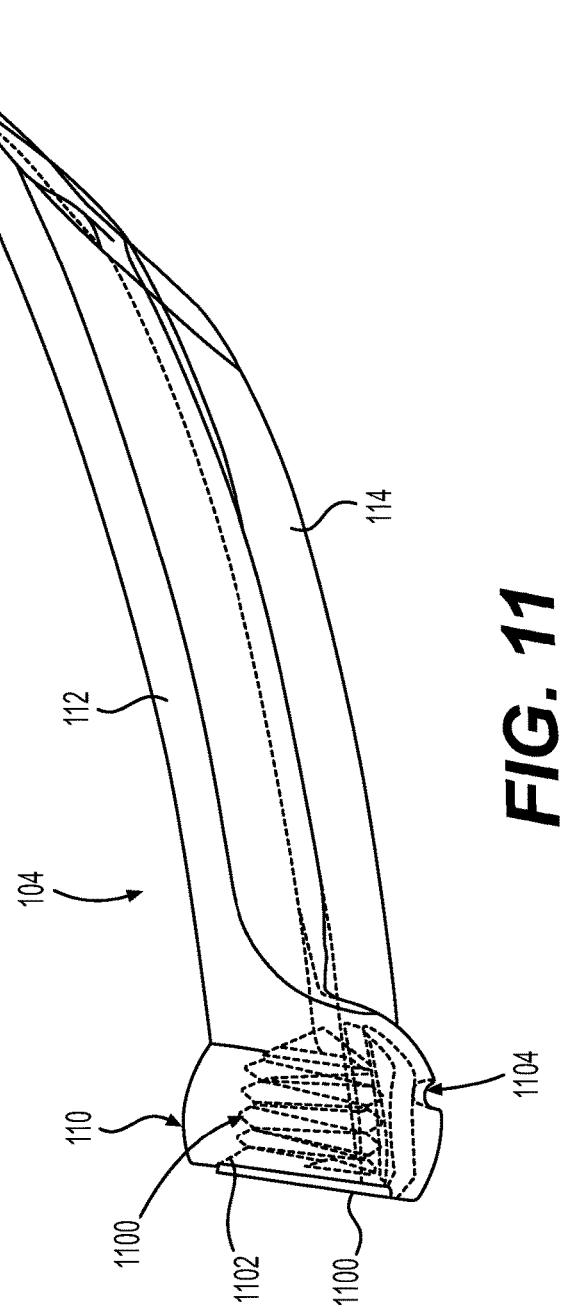

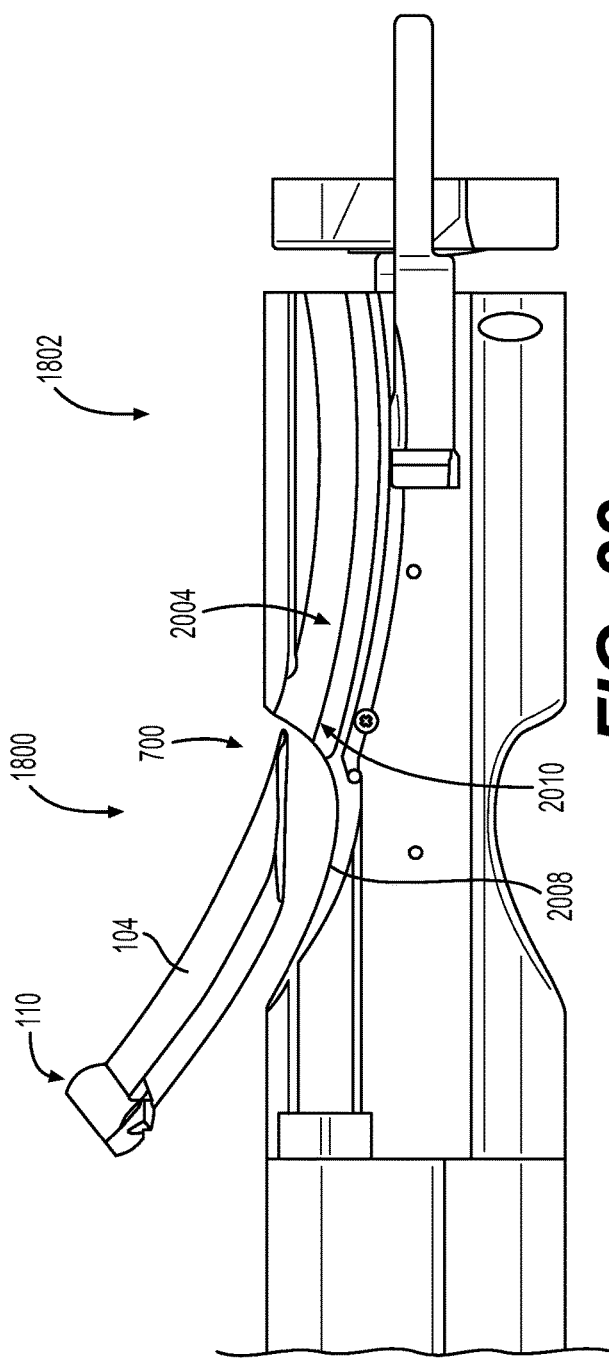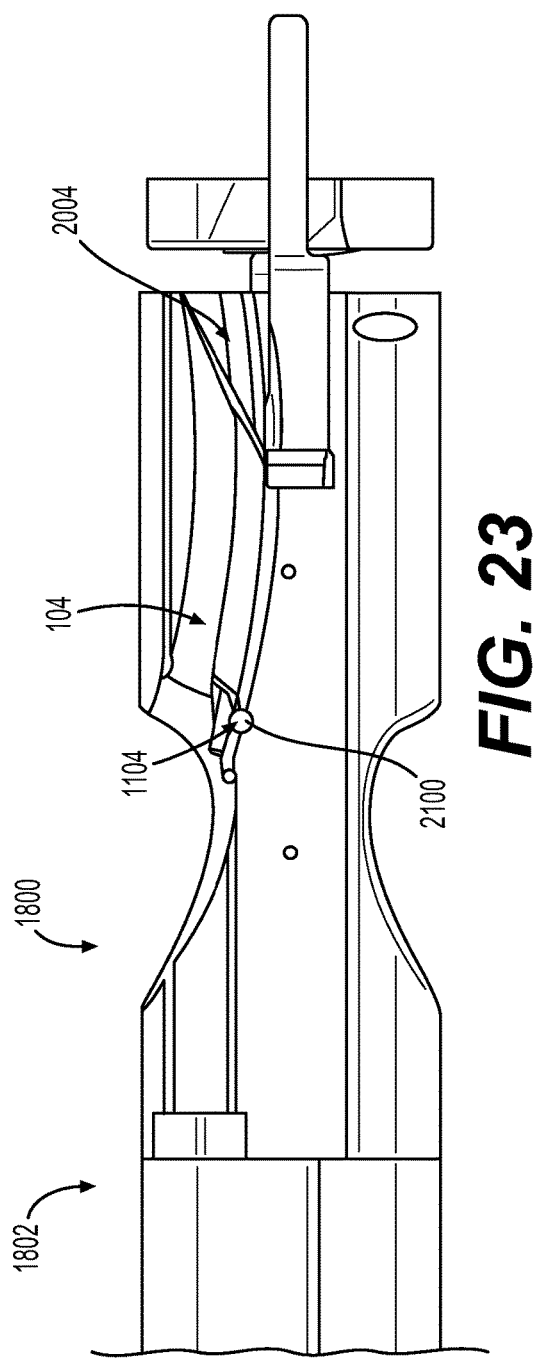

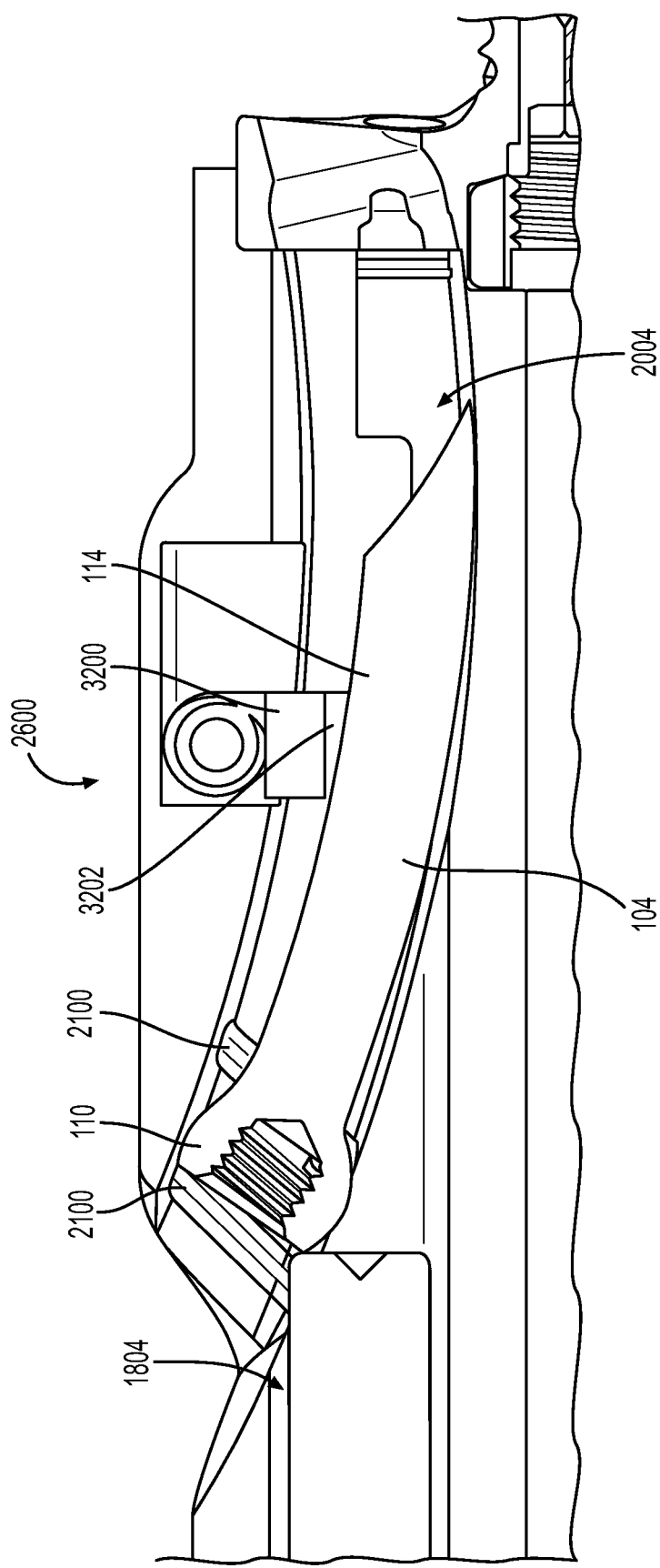

INTERVERTEBRAL IMPLANT SYSTEM FOR AN INLINE TECHNIQUE WITH PATIENT IN A LATERAL DECUBITUS POSITION

BACKGROUND

Intervertebral implants are used for stabilizing adjacent vertebrae of the spine. The implants are inserted between adjacent vertebra of the spine and adjusted based on the condition of the spine. Generally, the implants are secured between the adjacent vertebrae via fastening devices (e.g., anchors, screws). However, during a lateral approach interbody fusion with a patient on their side in a lateral decubitus position, the ribs and iliac crest can cause interference when accessing the levels L1-S1. This interference can incur challenges when implanting and/or securing the implant. Using curved fasteners may alleviate some of the issues associated with such challenges by eliminating the need for angled instrumentation. However, implementing curved fasteners may present its own unique challenges with regard to alignment, insertion, and efficacy. Improvements to curved fasteners, as well as to insertion devices and other instrumentation may provide a simpler, more intuitive, more efficient surgical implant system for a lateral approach interbody fusion with a patient on their side in a lateral decubitus position.

BRIEF DESCRIPTION OF THE DRAWINGS

These drawings illustrate certain aspects of some of the embodiments of the present invention and should not be used to limit or define the invention.

FIG. 10 illustrates a side view of the anchor, in accordance with embodiments of the present disclosure.

FIG. 11 illustrates a cross-sectional view of the anchor, in accordance with embodiments of the present disclosure.

FIG. 22 illustrates a cross-sectional view of the surgical implant system with the anchor loading into the anchor loading chamber of the insertion device, in accordance with embodiments of the present disclosure.

FIG. 23 illustrates a cross-sectional view of the surgical implant system with the anchor loaded in the anchor loading chamber of the insertion device, in accordance with embodiments of the present disclosure.

FIG. 33 illustrates a cross-sectional view of the impactor entering the single anchor insertion device, in accordance with embodiments of the present disclosure.

DETAILED DESCRIPTION

It is to be understood that the present disclosure is not limited to particular systems, devices, and/or methods, which may, of course, vary. It is also to be understood that the terminology used herein is for the purpose of describing particular embodiments only and is not intended to be limiting. All numbers and ranges disclosed herein may vary by some amount. Whenever a numerical range with a lower limit and an upper limit is disclosed, any number and any included range falling within the range are specifically disclosed. Although individual embodiments are discussed herein, the invention covers all combinations of all those embodiments. As used herein, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected. If there is any conflict in the usages of a word or term in this specification and one or more patent or other documents that may be incorporated herein by reference, the definitions that are consistent with this specification should be adopted for the purposes of understanding this invention.

Figure 1:
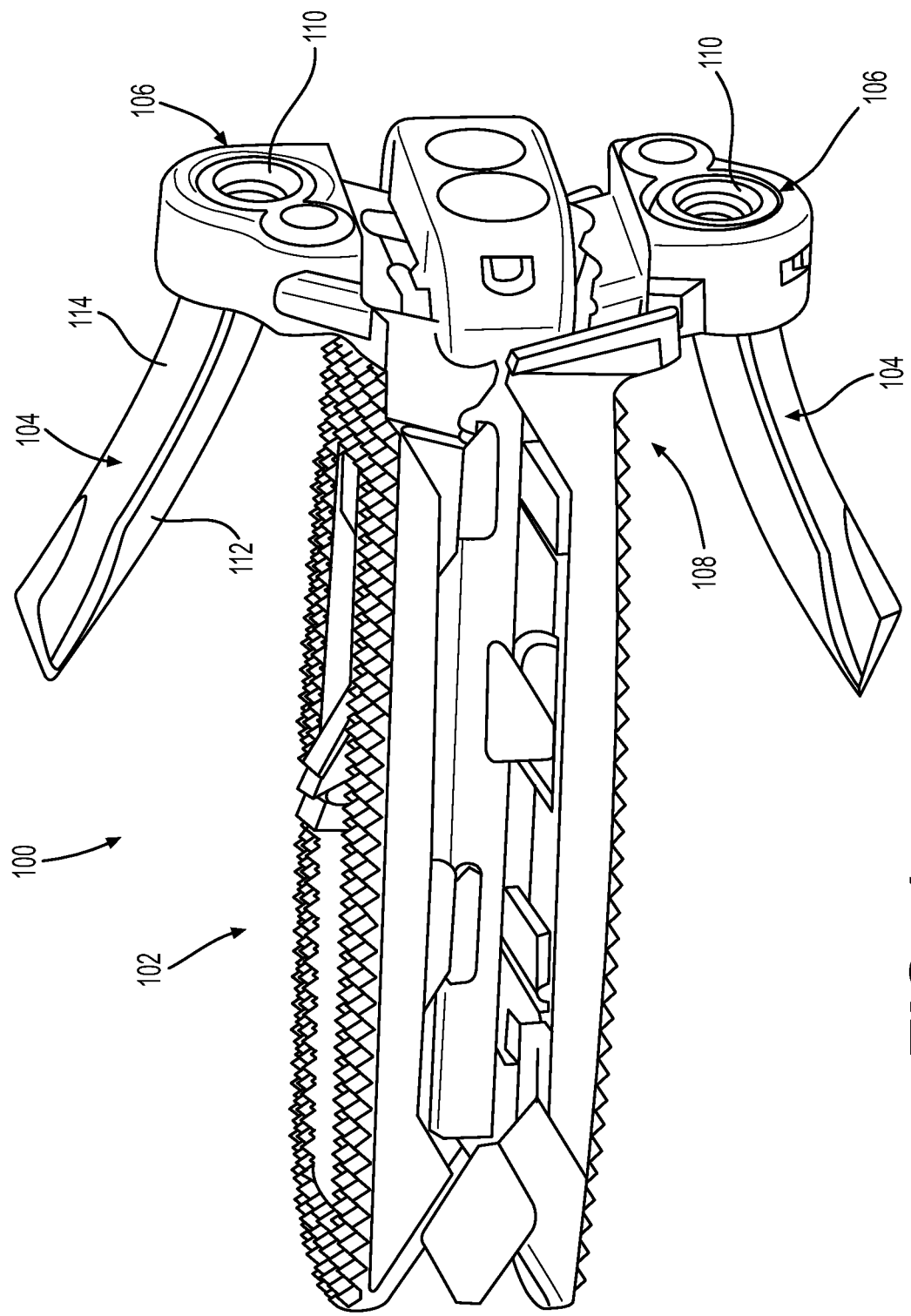
FIG. 1 illustrates a perspective view of a surgical implant having a spacer with anchor fixation, in accordance with embodiments of the present disclosure.

Referring now to the drawings, FIG. 1 illustrates a perspective view of a surgical implant 100 having a spacer 102 with anchor 104 fixation. The spacer 102 may be an expandable lumber interbody spacer 102 (ELSA) securable, via a plurality of anchors 104 (e.g., curvilinear fastening elements), within an intervertebral space defined by adjacent vertebral bodies of a spine. The spacer 102 may be used to provide structural stability to the adjacent vertebral bodies. The spacer 102 includes a plurality of eyelets 106 (e.g., bores) configured to receive corresponding anchors 104. During insertion, the anchors 104 may be inserted through the eyelets 106 and into corresponding adjacent vertebral bodies. The anchors 104 may hinder migration of the spacer 102 with respect to the adjacent vertebral bodies. Further, securing the anchors 104 to the corresponding adjacent vertebral bodies may rigidly secure the adjacent vertebral bodies to each other (e.g., for spinal fusion) due to the rigidity of the surgical implant 100.

The spacer 102 may include any suitable material for fusion between adjacent vertebral bodies (e.g., physiologically compatible material). For example, the spacer 102 may include a Polyether ether ketone (PEEK) material. Further, the spacer 102 may include tantalum marker pins (not shown) having strong radiographic opacity for X-ray marking purposes. Additionally, the spacer 102 may include a plurality of moveable actuators 108 configured to move in response to mechanical input to expand the surgical implant 100 to a position for supporting the adjacent vertebral bodies.

Moreover, the plurality of anchors 104 for securing the spacer 102 to the vertebral bodies may be curved. In particular, each anchor 104 may include a head portion 110 with an elongate shank 112 and elongate fin 114 extending from the head portion 110 in a direction substantially toward a tip of the anchor 104. The elongate shank 112 and the elongate fin 114 may extend along a curved profile. Having curved anchors 104 may allow for insertion of the spacer 102 and anchors 104 using non-angled instrumentation. An amount of curve (e.g., radius of curvature, trajectory) may be based at least in part on an optimal approach angle to the spine where the angled instrumentation would have ensured that the attachment angle and the angle of fixation are identical, such that fixation is delivered through the same trajectory.

Figure 2:
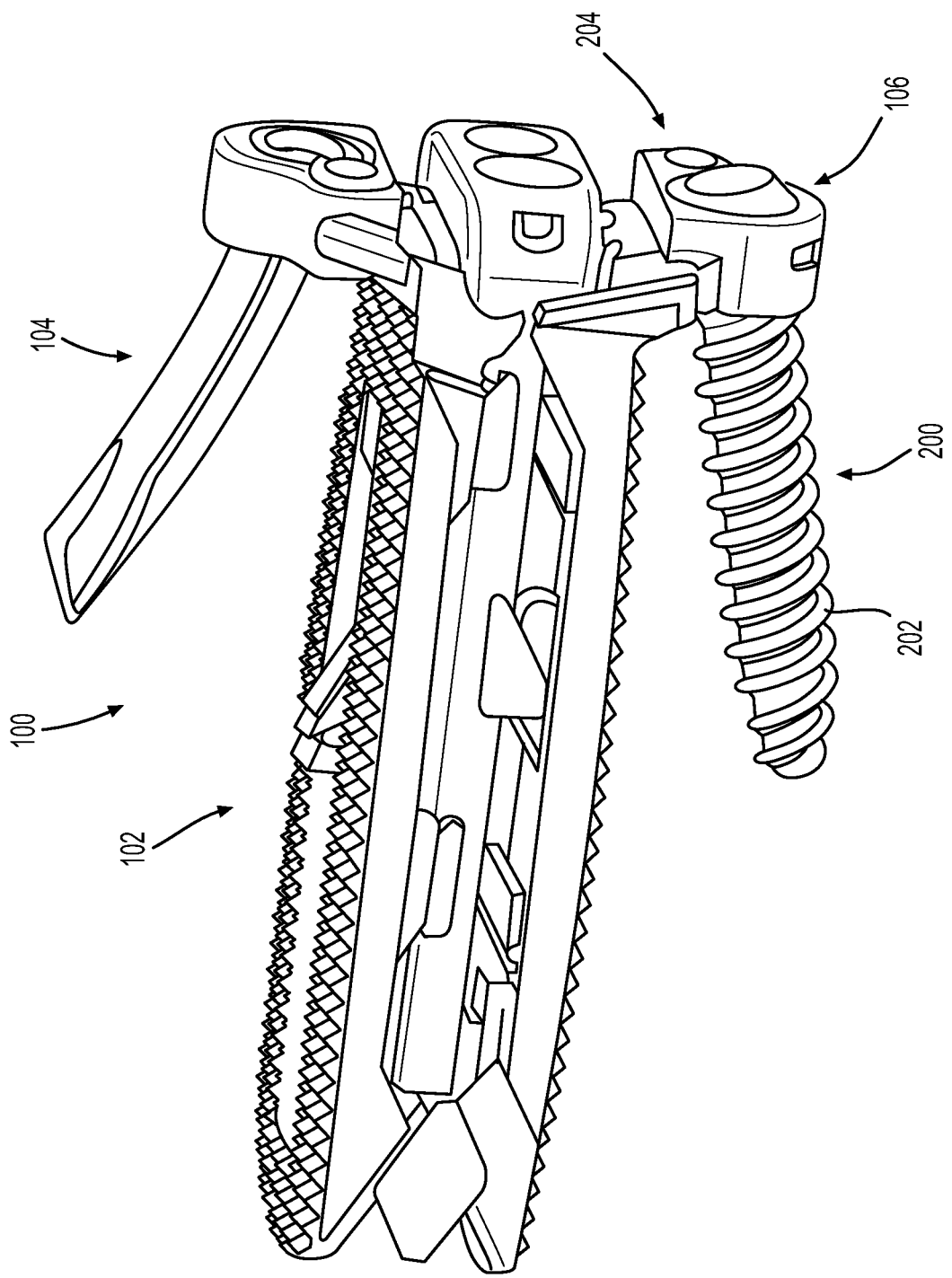
FIG. 2 illustrates a perspective view of a surgical implant spacer having hybrid fixation, in accordance with embodiments of the present disclosure.

FIG. 2 illustrates a perspective view of a surgical implant 100 having the spacer 102 secured via hybrid fixation, in accordance with embodiments of the present disclosure. That is, the spacer 102 may be secured to the adjacent vertebral bodies via at least one anchor 104 and at least one screw 200. The at least one screw 200 may be inserted through at least one of the plurality of eyelets 106 of the spacer 102 and into a corresponding vertebral body. Further, the at least one screw 200 may include threading 202 to resist forces on the at least one screw 200 urging the at least one screw 200 to back out of the osteotomy formed in the vertebral body via insertion of the at least one screw 200.

In some embodiments, the surgical implant 100 may include a blocking member 204 mounted to a portion of the spacer 102. After insertion of the at least one anchor 104 and the at least one screw 200 through their respective eyelets 106, the blocking member 204 may be configured to move into a position (e.g., blocking position) over the eyelets 106 to prevent the at least one anchor 104 and/or the at least one screw 200 from retracting out through the respective eyelets 106. The blocking member 204 may be configured to contact respective head portions 110 of the at least one anchor 104 and the at least one screw 200 in the blocking position. Further, the blocking member 204 may be secured to sit flush with the spacer 102 in the blocking position.

Figure 3:
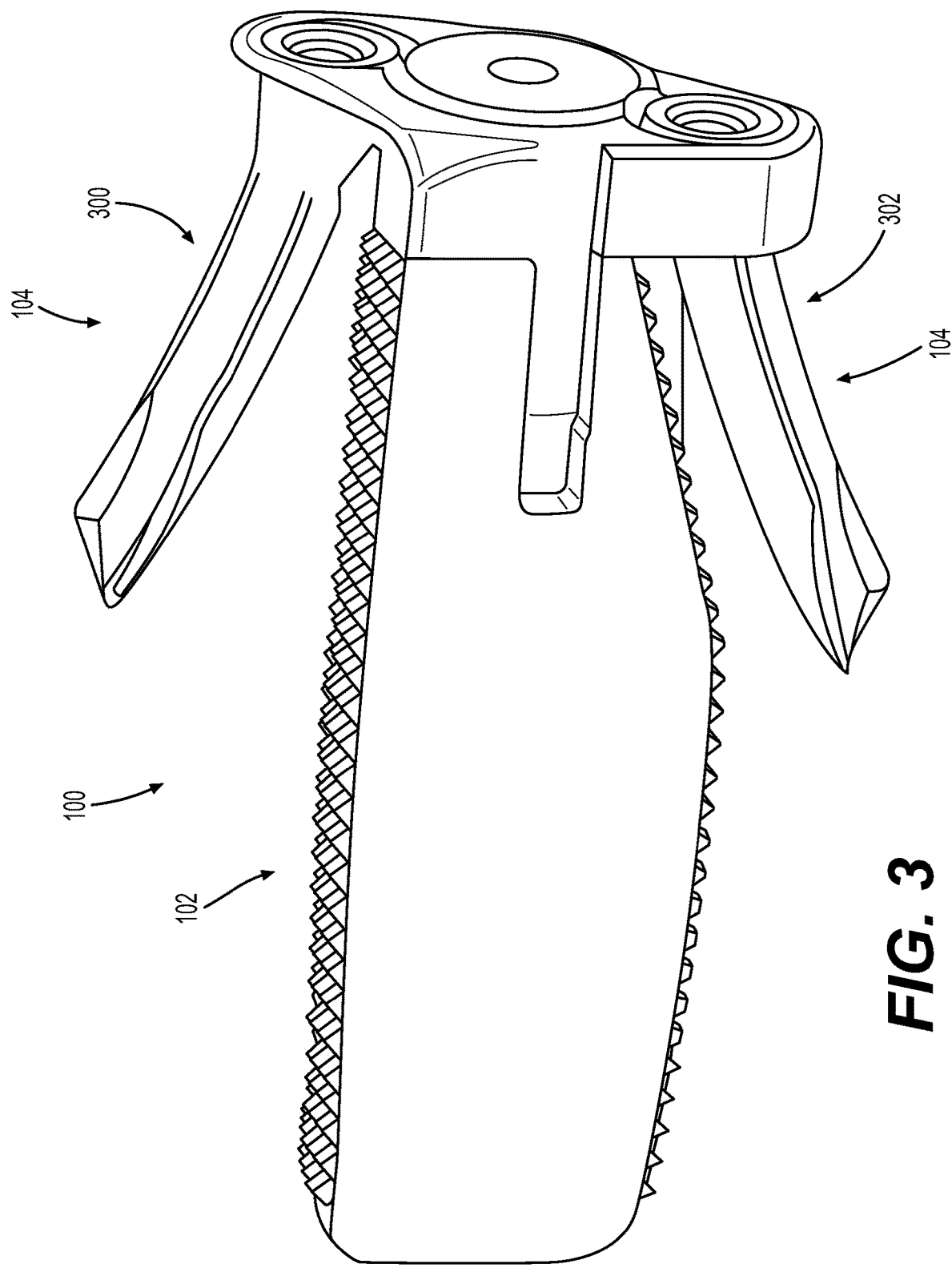
FIG. 3 illustrates a perspective view of a fixed surgical implant having the spacer, in accordance with embodiments of the present disclosure.

FIG. 3 illustrates a perspective view of a fixed surgical implant 100 having the spacer 102, in accordance with embodiments of the present disclosure. The fixed surgical implant 100 having the spacer 102 may be configured for lateral insertion into the space between the adjacent vertebral bodies. The fixed surgical implant 100 having the spacer 102 may be secured to the adjacent vertebral bodies via the plurality of anchors 104 (e.g., the first anchor 300 and the second anchor 302).

Figure 4:
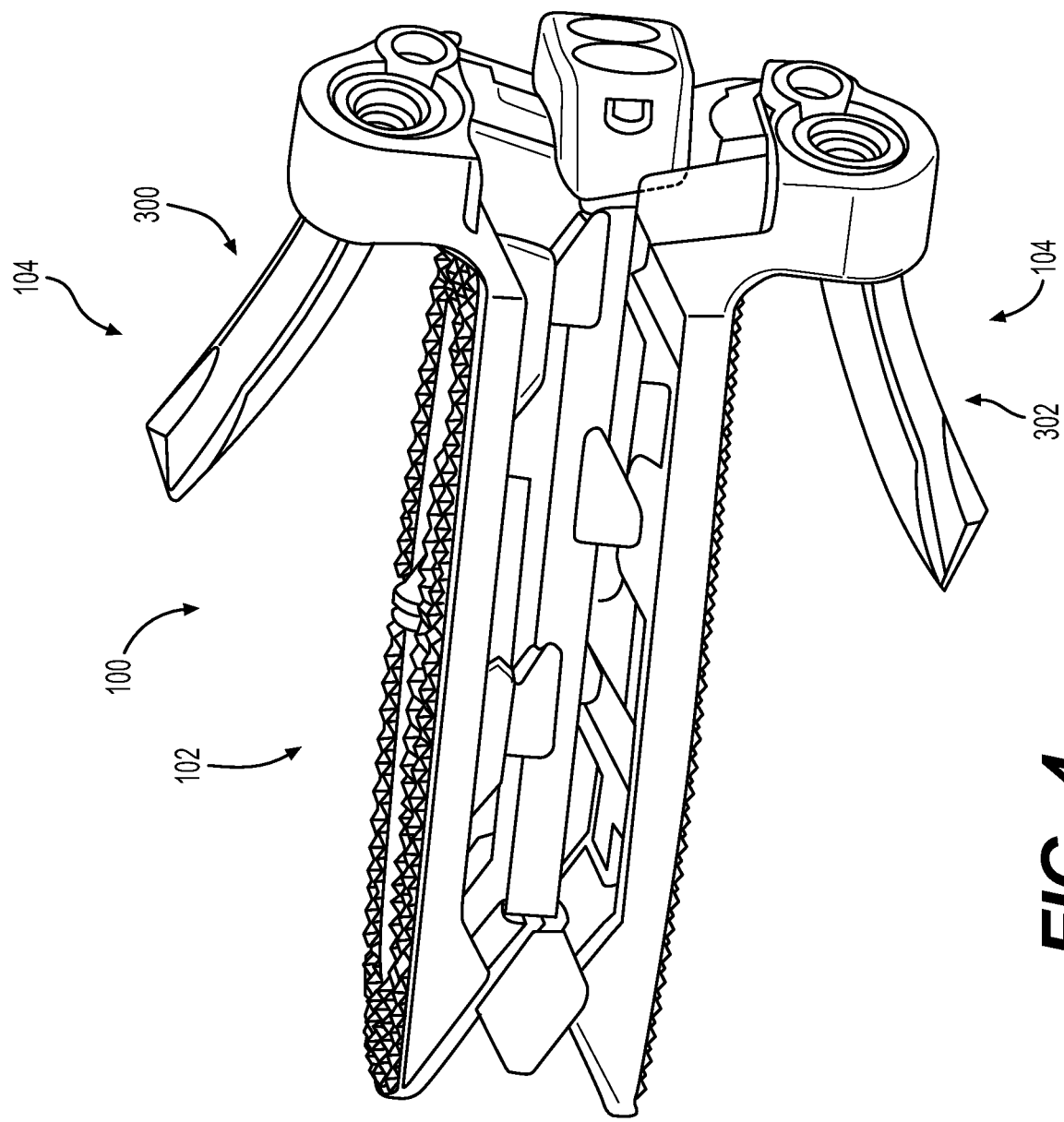
FIG. 4 illustrates a perspective view of an expandable surgical implant having the spacer, in accordance with embodiments of the present disclosure.

FIG. 4 illustrates a perspective view of an expandable surgical implant 100 having the spacer 102, in accordance with embodiments of the present disclosure. The spacer 102 may be an expandable anterior-to-psoas lumber interbody spacer 102 with integrated fixation. The spacer 102 may be configured for lateral insertion into the spine between the adjacent vertebral bodies. Moreover, the spacer 102 may be secured to the adjacent vertebral bodies via the plurality of anchors 104 (e.g., the first anchor 300 and the second anchor 302).

Figure 5:
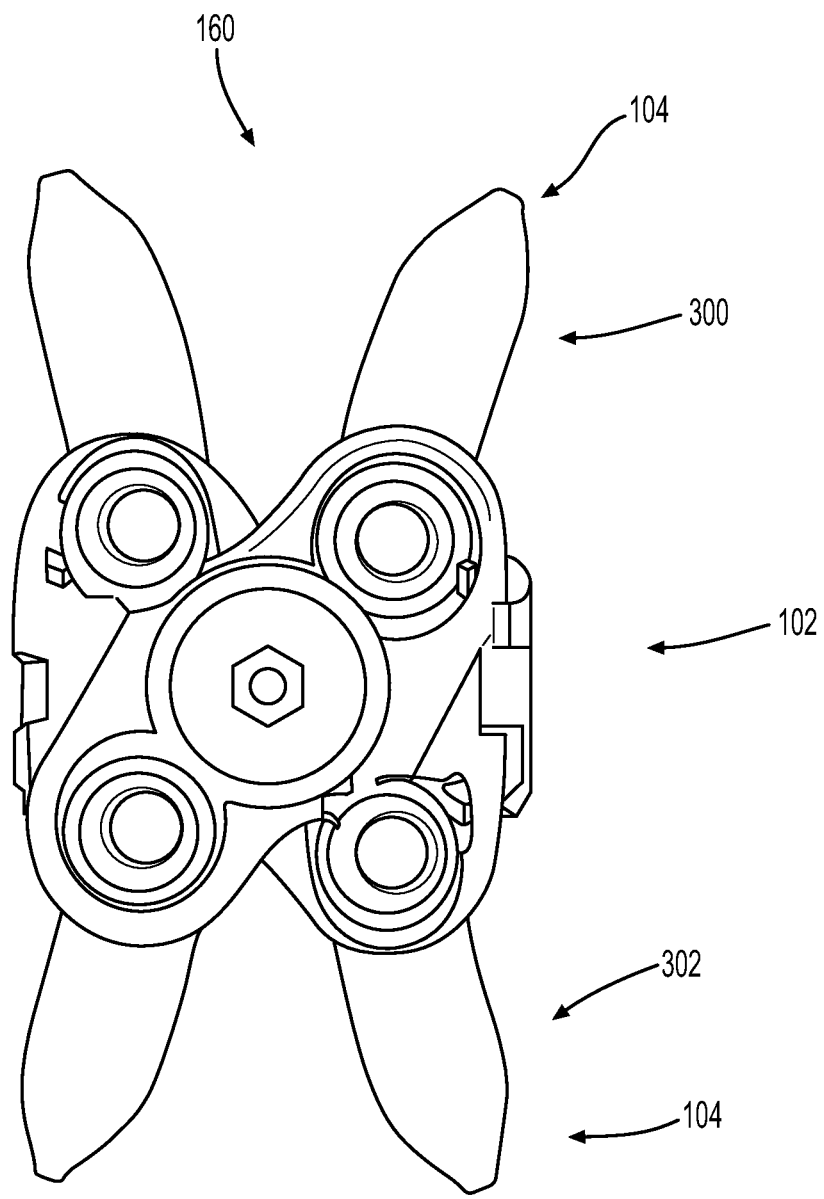
FIG. 5 illustrates a perspective view of a surgical implant having the spacer with divergent anchor fixation, in accordance with embodiments of the present disclosure.

FIG. 5 illustrates a perspective view of a surgical implant 100 having the spacer 102 with divergent anchor fixation, in accordance with embodiments of the present disclosure. The surgical implant 100 comprises the plurality of anchors 104 configured to secure the spacer 102 to the adjacent vertebral bodies. In some embodiments, the plurality of anchors 104 may include the first anchor 300 and the second anchor 302. As illustrated, the first anchor 300 and the second anchor 302 are configured for insertion into their respective vertebral bodies at divergent orientations with respect to each other. Divergent anchor 104 placement may provide additional rotational stability.

Figure 6:
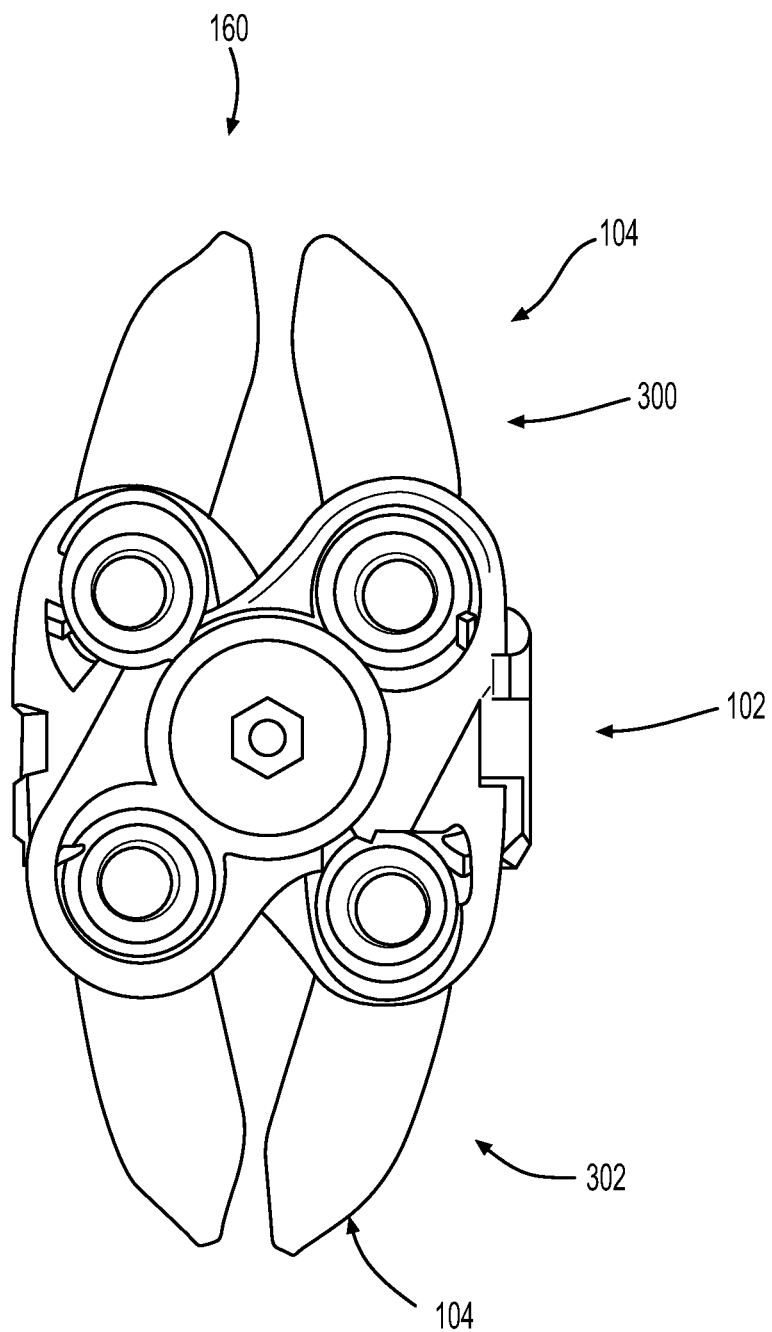
FIG. 6 illustrates a perspective view of a surgical implant having the spacer with convergent anchor fixation, in accordance with embodiments of the present disclosure.

FIG. 6 illustrates a perspective view of a surgical implant 100 having the spacer 102 with convergent anchor fixation, in accordance with embodiments of the present disclosure. In the illustrated embodiment, the first anchor 300 and the second anchor 302 are configured for insertion into their respective vertebral bodies at convergent orientations with respect to each other. Convergent anchor 104 placement may provide variability to accommodate supplemental posterior fixation.

Figure 7:
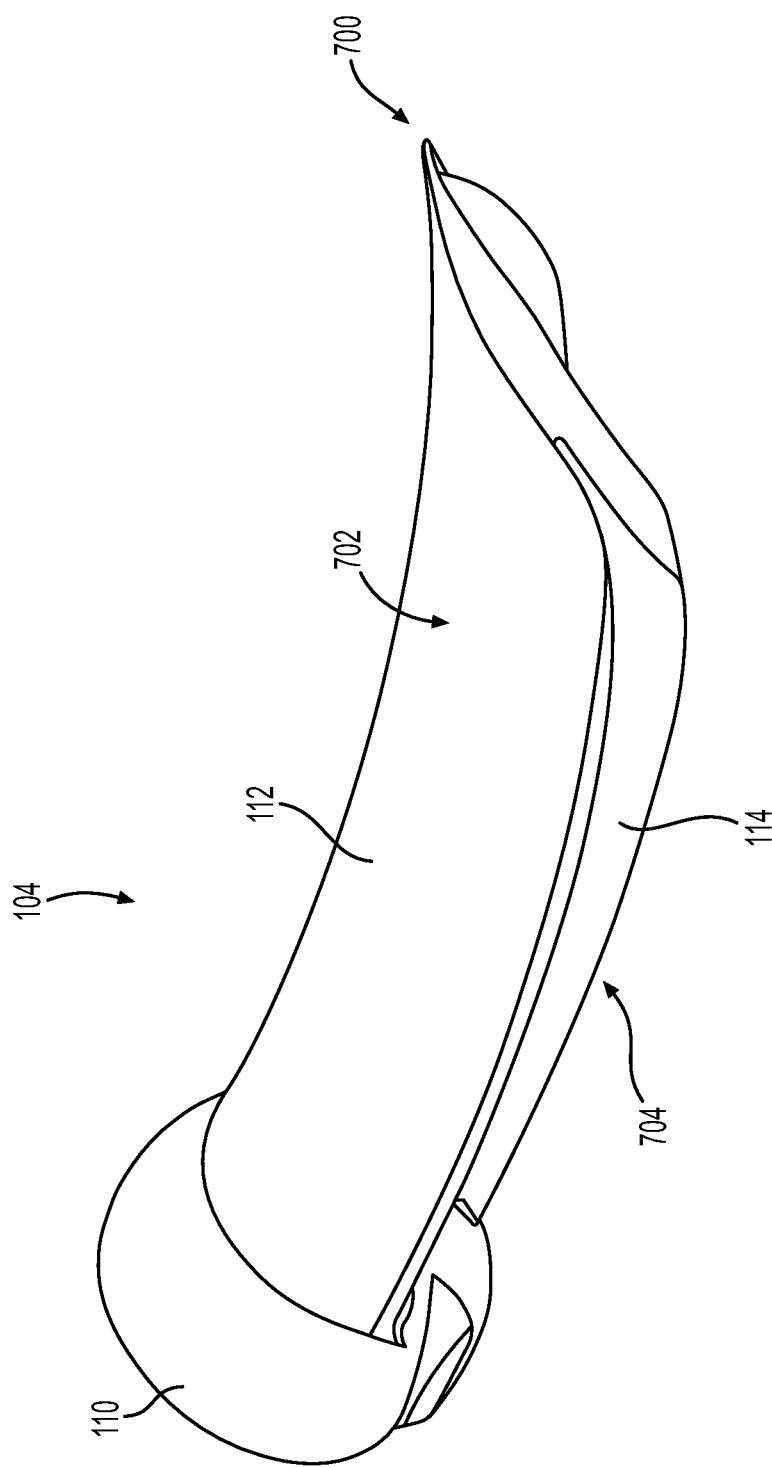
FIG. 7 illustrates a perspective view of the anchor, in accordance with embodiments of the present disclosure.

FIG. 7 illustrates a perspective view of the anchor 104, in accordance with embodiments of the present disclosure. As set forth above, the anchor 104 includes the head portion 110 with the elongate shank 112 and the elongate fin 114 extending from the head portion 110 in a direction substantially toward a tip portion 700 of the anchor 104. The elongate shank 112 and the elongate fin 114 may extend along a curved profile. In some embodiments, a trajectory of the curved profile may be between five and fifteen degrees. In the illustrated embodiment, the curved profile has a twelve-degree trajectory. Further, the trajectory may span across lateral integrated cages of the surgical implants 100.

Moreover, the anchor 104 comprises a concave side 702 and a convex side 704. In the illustrated embodiment, the concave side 702 of the anchor 104 is formed along an outer top surface the elongate shank 112 and the convex side 704 formed along an outer bottom surface of the elongate fin 114. The concave side 702 and the convex side 704 may be disposed on opposing sides of the anchor 104. Further, in the illustrated embodiment, the tip portion 700 of the anchor 104 is positioned on the concave side 702 of the anchor 104 at the end of the elongate shank 112. However, in some embodiments, the tip portion 700 may be formed on the convex side 704 of the anchor 104.

Figure 8:
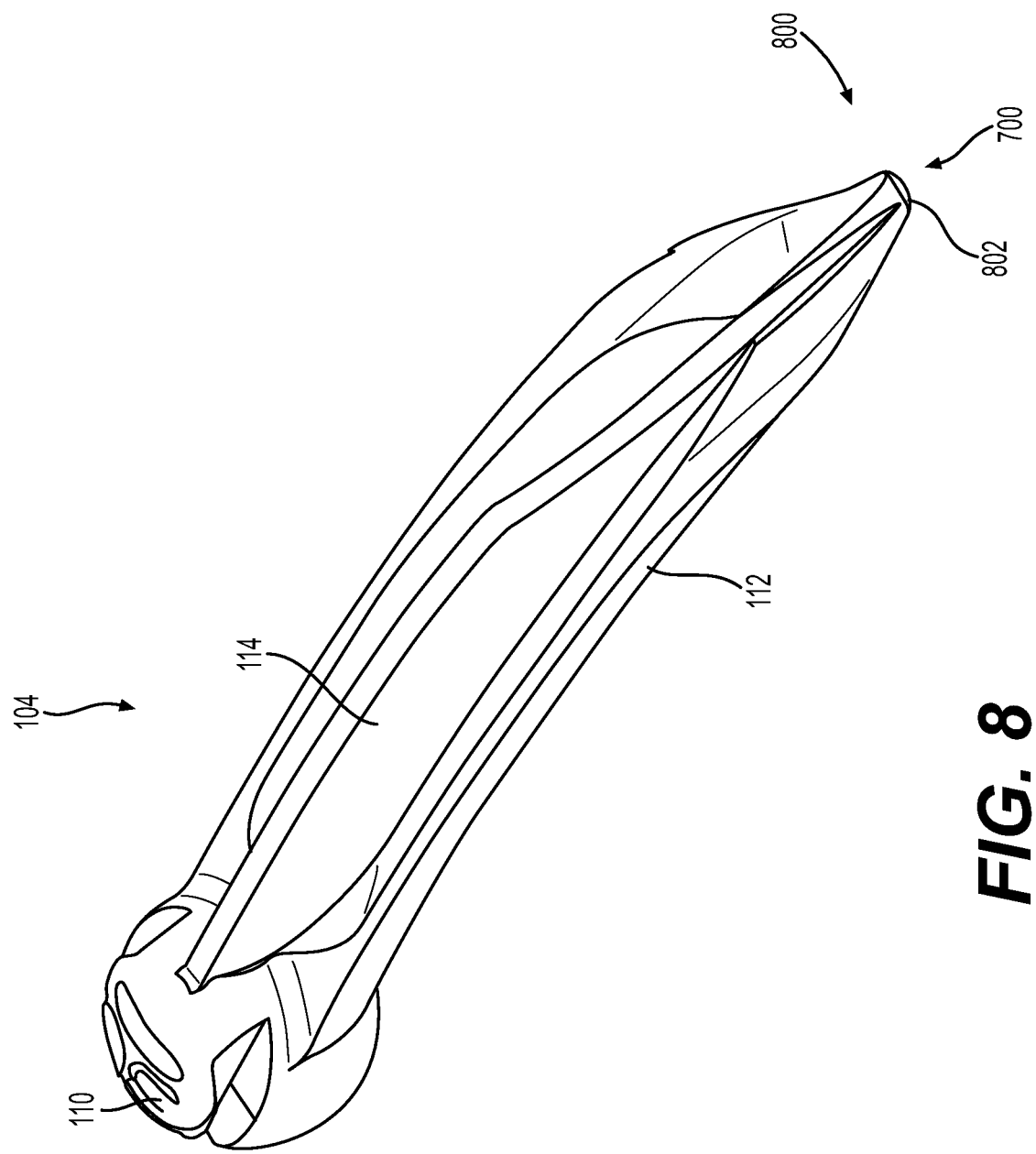
FIG. 8 illustrates another perspective view of the anchor, in accordance with embodiments of the present disclosure.

FIG. 8 illustrates another perspective view of the anchor 104, in accordance with embodiments of the present disclosure. As set forth above, the anchor 104 may be configured for insertion through the at least one implant eyelet 106 of the spacer 102 (shown in FIG. 1) to fasten the spacer 102 to a vertebral body of the spine. The anchor 104 includes the head portion 110 with the elongate shank 112 extending from the head portion 110. Further, the elongate fin 114 extends from the head portion 110 and along a surface of the elongate shank 112. Together, the elongate shank 112 and the elongate fin 114 form a curved t-shaped cross-section along a profile of the anchor 104. The curved T-shaped cross section may maximize strength and rigidity, while reducing the overall profile of the anchor 104 in the bone (e.g., vertebral body). A majority of the cross-sectional surface area of the anchor 104 passing through the bone may be located away from an endplate of the vertebral body being operated on, so that vertical translation of the anchor 104 is away from the endplate.

Moreover, the tip portion 700 of the anchor 104 may be tapered for easier insertion into the vertebral body. In the illustrated embodiment, a distal end 800 of the elongate shank 112 is tapered to form the tip portion 700. Further, the elongate fin 114 is tapered proximate the tip portion 700. However, a tip end 802 of the tip portion 700 may not be tapered. Without a sharpened tip end 802, the anchor 104 (e.g., elongate shank 112 and/or elongate fin 114) may include a double beveled profile proximate the distal end 800 of the elongate shank 112 to effectively penetrate the vertebral body. Indeed, the double beveled profile may reduce a cross-sectional area of the anchor 104 entering the vertebral body such that the anchor 104 may effectively penetrate the vertebral body.

Figure 9:
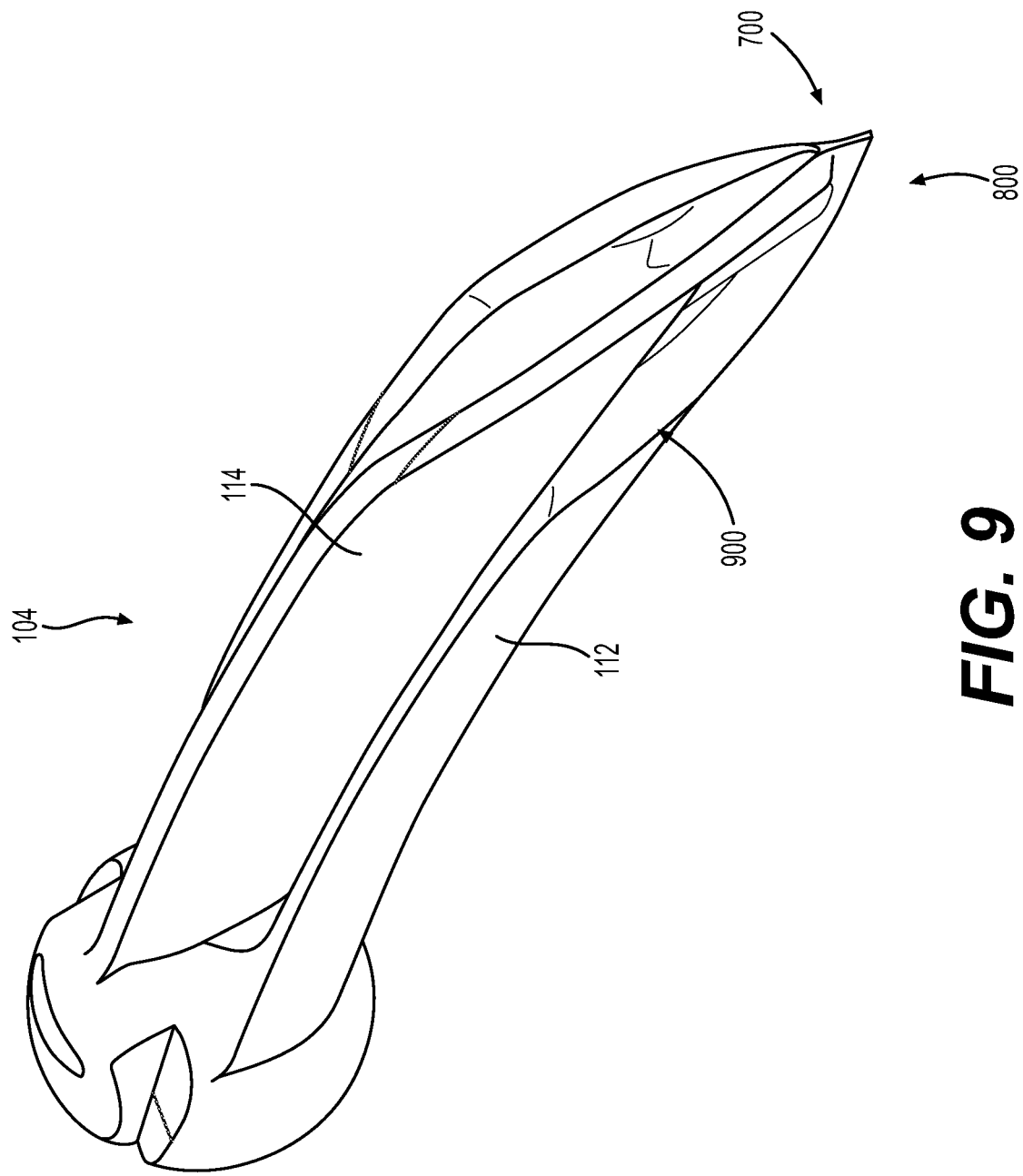
FIG. 9 illustrates a perspective view of the anchor, in accordance with embodiments of the present disclosure.

FIG. 9 illustrates a perspective view of the anchor 104, in accordance with embodiments of the present disclosure. The anchor 104 may include sharpened serrations 900 proximate the tip portion 700 of the anchor 104. In the illustrated embodiment, the elongate shank 112 includes sharpened serrations 900 proximate the distal end 800 of the elongate shank 112. In some embodiments, the elongate fin 114 may include the sharpened serrations 900. The sharpened serrations 900 may enter uneven inconsistent surface of the vertebral body to ensure bone penetration by the anchor 104.

FIG. 10 illustrates a side view of the anchor 104, in accordance with embodiments of the present disclosure. As set forth above, the anchor 104 is configured to insertion through a corresponding eyelet 106 of the spacer 102 (shown in FIG. 1) and into a corresponding vertebral body. However, the head portion 110 of the anchor 104 does not pass through the eyelet 106. Instead, the head portion 110 of the anchor 104 may be seated on the eyelet 106. In some embodiments, the head portion 110 may be configured to sit flush with a plate of the spacer 102 housing the eyelet 106 such that the head portion 110 does not protrude out from the plate. As such, the head portion 110 may include an angled face 1000 formed via a seventy-five to eighty-five degree flat cut 1002 into the head portion 110. In the illustrated embodiment, the angled face 1000 is formed via a 780 flat cut into the head portion 110 such that the head portion 110 may sit flush with plate of the surgical implant.

FIG. 11 illustrates a cross-sectional view of the anchor 104, in accordance with embodiments of the present disclosure. As illustrated, the head portion 110 includes a threaded counterbore 1100 extending into the angled face 1000 in a direction toward the elongate shank 112 and the elongate fin 114. The threaded counterbore 1100 may be included for implant removal purposes. Further, a portion of the threaded counterbore 1100 proximate the angled face 1000 may include a chamfer 1102. The chamfer 1102 may help prevent thread interference after insertion. Moreover, the anchor 104 may also include a hole feature 1104 configured to interface with an insertion device 1802 (shown in FIG. 18) to provide temporary containment of anchor 104 within the insertion device 1802.

Figure 12:
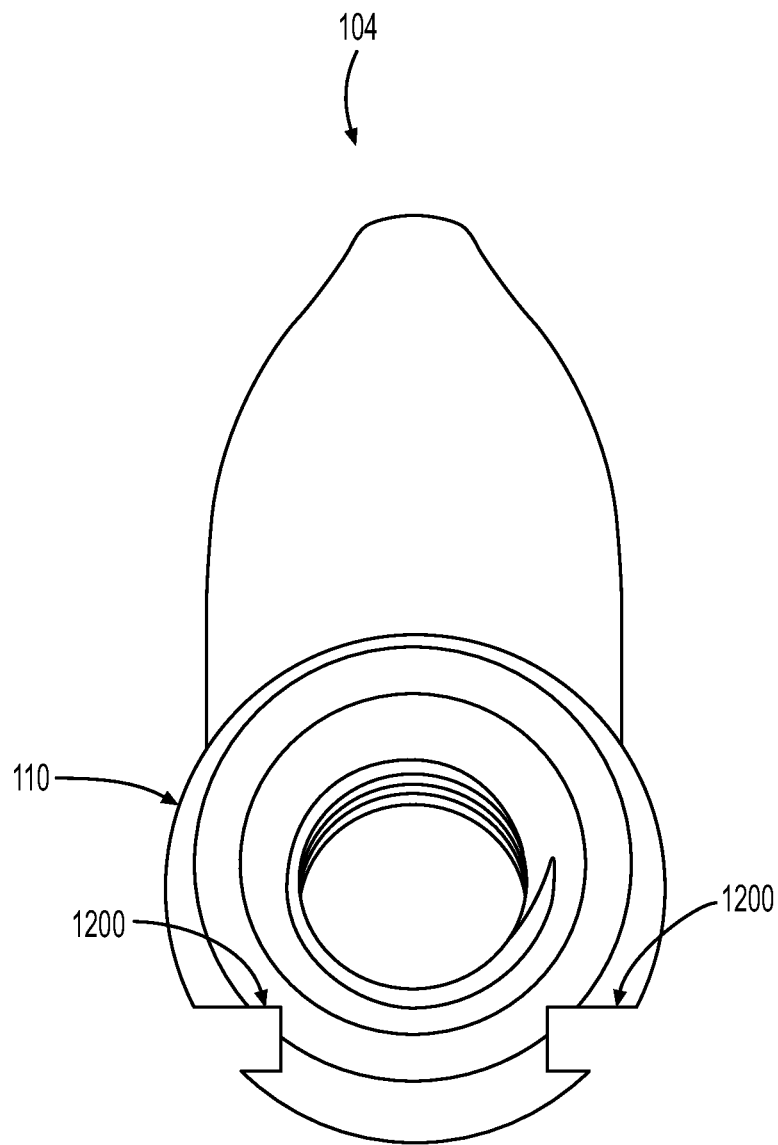
FIG. 12 illustrates an orthogonal view of the anchor, in accordance with embodiments of the present disclosure.

FIG. 12 illustrates an orthogonal view of the anchor 104, in accordance with embodiments of the present disclosure. As illustrated, the head portion 110 includes key cut features 1200 configured to interface with the insertion device 1802 (shown in FIG. 18) to restrain rotation of the anchor 104 during insertion. Further, the key cut features 1200 may restrain vertical and horizontal motion during insertion. In some embodiments, the key cut features 1200 may include a height between 0.6-0.10 millimeters. Moreover, the key cut features 1200 may be positioned to reduce a risk of sticking and/or jamming of the anchor 104 within the insertion device 1802 during insertion of the anchor 104 into the insertion device 1802.

Figure 13:
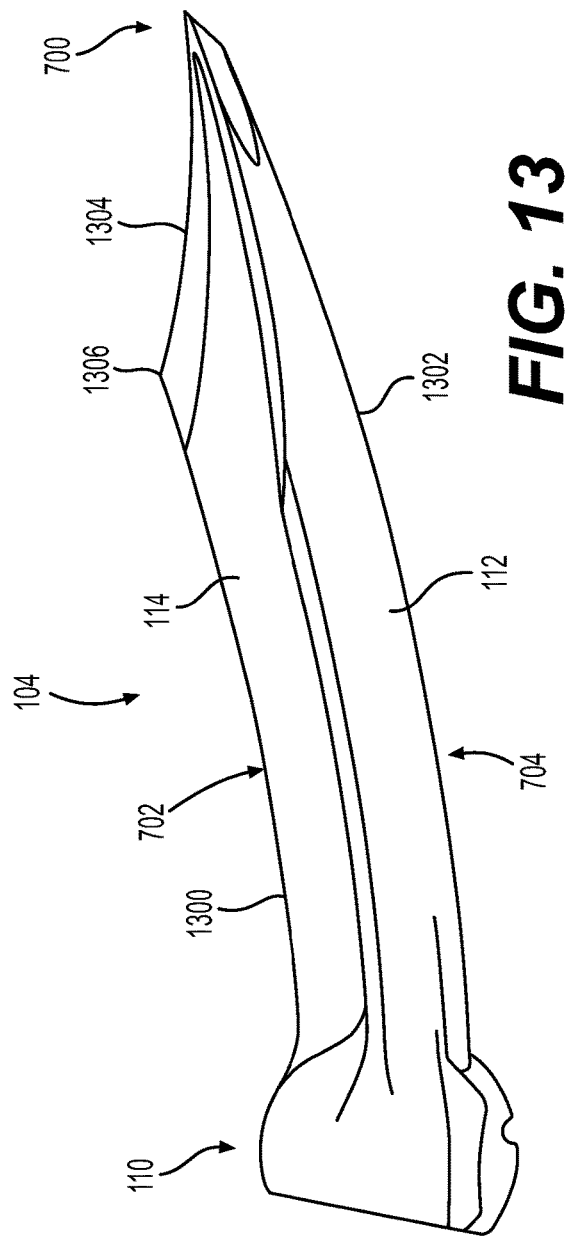
FIG. 13 illustrates a side view of the anchor, in accordance with embodiments of the present disclosure.

FIG. 13 illustrates a side view of the anchor 104, in accordance with embodiments of the present disclosure. As set forth above, the anchor 104 includes the head portion 110 with the elongate shank 112 extending from the head portion 110. Further, the elongate fin 114 extends from the head portion 110 and along a surface of the elongate shank 112. In the illustrated embodiment, the elongate shank 112 and the elongate fin 114 form an inverted curved t-shaped cross-section along the profile of the anchor 104. The curved T-shaped cross section may maximize strength and rigidity, while reducing the overall profile of the anchor 104 in the bone (e.g., vertebral body). Further, the elongate shank 112 and the fin may form a duckbill shaped cross-section at the tip portion 700 of the anchor 104.

Moreover, the anchor 104 comprises the concave side 702 and the convex side 704. In the illustrated embodiment, the concave side 702 of the anchor 104 is formed along an outer top surface 1300 the elongate fin 114 and the convex side 704 formed along an outer bottom surface 1302 of the elongate shank 112. The concave side 702 and the convex side 704 may be disposed on opposing sides of the anchor 104. Further, in the illustrated embodiment, the tip portion 700 of the anchor 104 is positioned on the convex side 704 of the anchor 104 at the end of the elongate shank 112.

An end portion 1304 of the anchor 104 may extend between the tip portion 700 (e.g., the convex side 704 of the anchor 104 at the end of the elongate shank 112) and a distal end 1306 of the concave side 702 of anchor 104 at the end of the elongate fin 114. The end portion 1304 may be concave. However, in some embodiments, the end portion 1304 may be straight or convex. The end portion 1304 is configured to penetrate portions of the vertebral body disposed upward with respect to the anchor 104. The end portion 1304 may comprise a bevel to reduce cross-sectional area of the end portion 1304 to improve ease of penetration of the end portion 1304 into the vertebral body.

Figure 14:
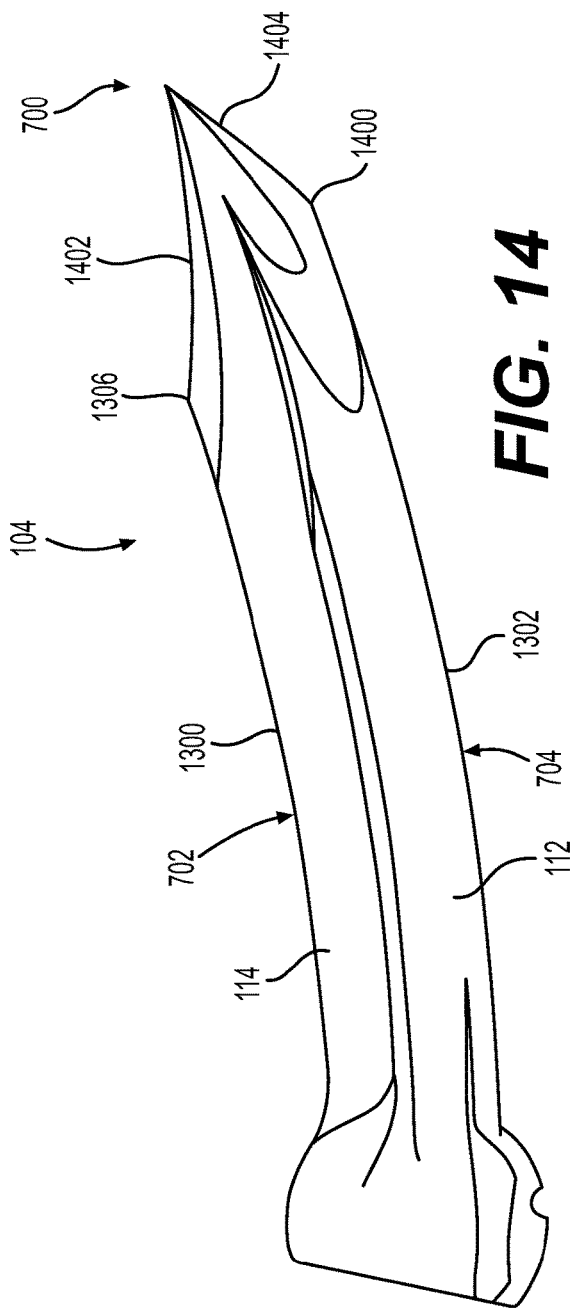
FIG. 14 illustrates a side view of the anchor, in accordance with embodiments of the present disclosure.

FIG. 14 illustrates a side view of the anchor 104, in accordance with embodiments of the present disclosure. As illustrated, the anchor 104 includes the concave side 702 of the anchor 104 formed along the outer top surface 1300 the elongate fin 114 and the convex side 704 formed along the outer bottom surface 1302 of the elongate shank 112. The tip portion 700 is positioned between a distal end 1400 of the convex side 704 of the anchor 104 at the end of the elongate shank 112 and the distal end 1306 of the concave side 702 of anchor 104 at the end of the elongate fin 114.

Further, the anchor 104 may include a first end portion 1402 and a second end portion 1404. The first end portion 1402 may extend between the tip portion 700 and the distal end 1306 of the concave side 702 of anchor 104 at the end of the elongate fin 114. The first end portion 1402 may be concave. However, the first end portion 1402 may include any suitable profile (e.g., straight, convex, serrated). The second end portion 1404 may extend between the tip portion 700 and the distal end of the convex side 704 of the anchor 104 at the end of the elongate shank 112. The second end portion 1404 may be convex. However, the second end portion 1404 may also include any suitable profile. Further, the first end portion 1402 and/or the second end portion 1404 may include a bevel to reduce cross-sectional area of the end portions 1304 to improve ease of penetration of the end portions 1304 into the vertebral body. Moreover, the tip portion 700, first end portion 1402, and second end portion 1404 may be configured to reduce skive from an extradiscal approach trajectory.

Figure 15B:
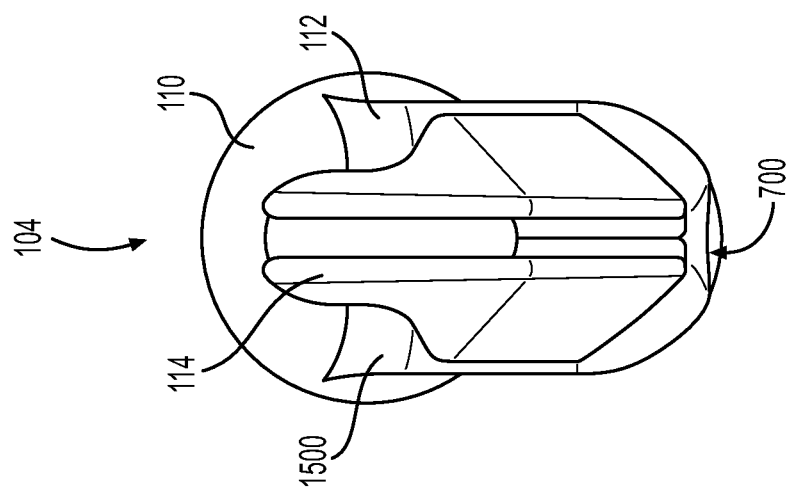
FIGS. 15A-15B illustrate orthogonal views of the anchor, in accordance with embodiments of the present disclosure.
Figure 15A:
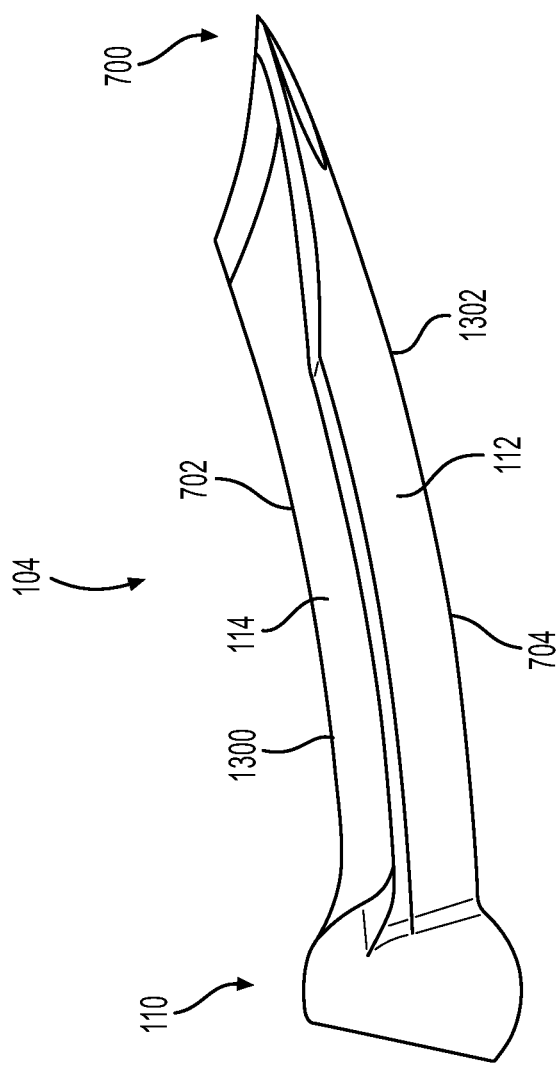

FIGS. 15A-15B illustrate orthogonal views of the anchor 104, in accordance with embodiments of the present disclosure. As illustrated in FIG. 15A, the anchor 104 includes the head portion 110 with the elongate shank 112 extending from the head portion 110. Further, the elongate fin 114 extends from the head portion 110 and along a surface 1500 of the elongate shank 112. As illustrated, the anchor 104 includes the concave side 702 of the anchor 104 formed along the outer top surface 1300 the elongate fin 114 and the convex side 704 formed along the outer bottom surface 1302 of the elongate shank 112. Further, the tip portion 700 of the anchor 104 is positioned on the convex side 704 of the anchor 104 at the end of the elongate shank 112. The tip portion 700 may be tapered for ease of insertion into a corresponding vertebral body. Referring to FIG. 15b, the tip portion 700 may include a duckbill shaped cross-section to minimize an amount (e.g., cross-sectional area) of material cutting through the vertebral body.

Figure 16B:
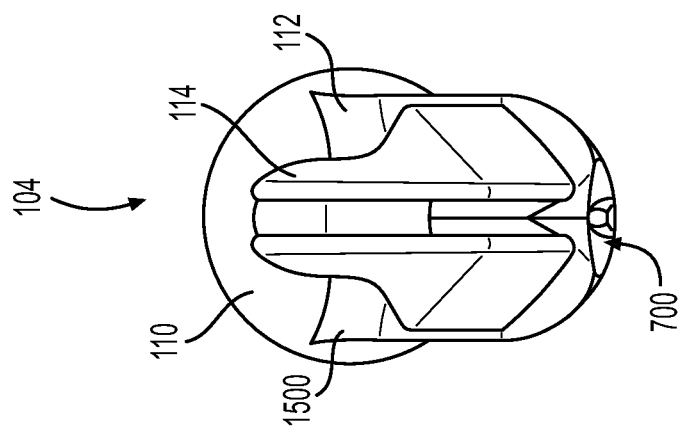
FIGS. 16A-16B illustrate orthogonal views of the anchor, in accordance with embodiments of the present disclosure.
Figure 16A:
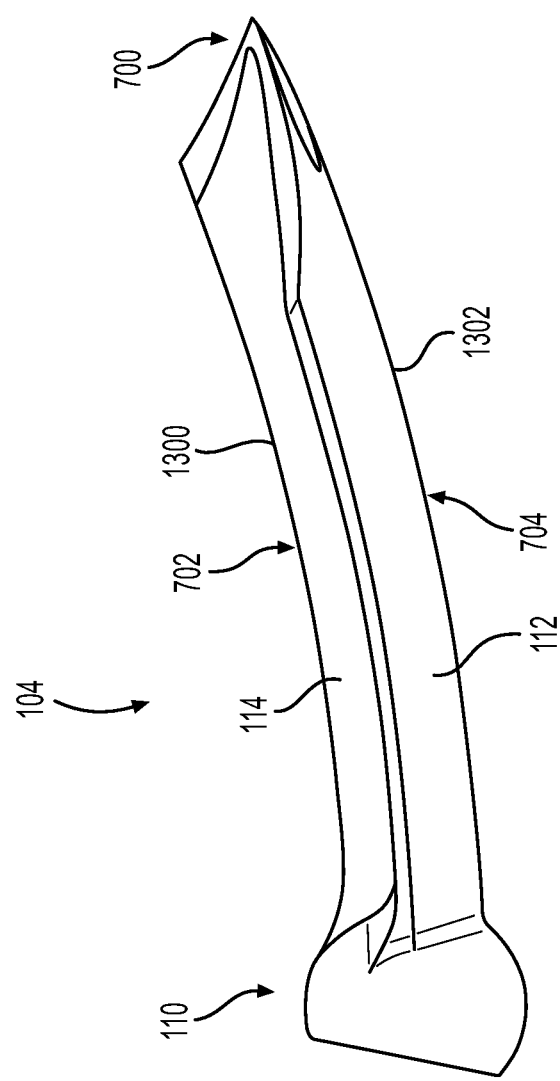

FIGS. 16A-16B illustrate orthogonal views of the anchor 104, in accordance with embodiments of the present disclosure. As illustrated in FIG. 16A, the anchor 104 includes the head portion 110 with the elongate shank 112 extending from the head portion 110. Further, the elongate fin 114 extends from the head portion 110 and along the surface 1500 of the elongate shank 112. As illustrated, the anchor 104 includes the concave side 702 of the anchor 104 formed along the outer top surface 1300 the elongate fin 114 and the convex side 704 formed along the outer bottom surface 1302 of the elongate shank 112. Further, the tip portion 700 of the anchor 104 is positioned on the convex side 704 of the anchor 104 at the end of the elongate shank 112. Referring to FIG. 16B, the tip portion 700 may be tapered such that the tip portion 700 of the anchor 104 becomes tangent to multiple areas of the spacer 102 (shown in FIG. 1) to ease insertion and ensure the proper trajectory of the anchor 104 into a corresponding vertebral body.

Figure 17B:
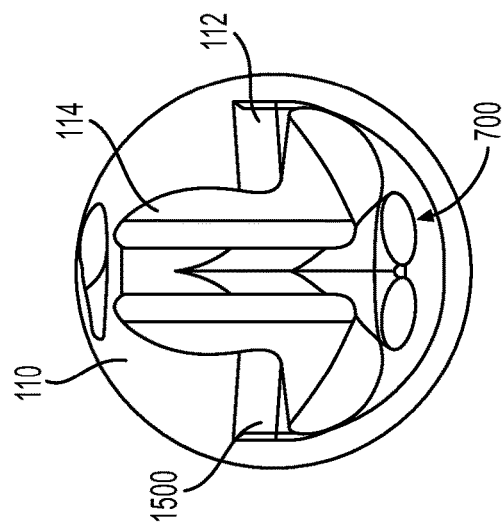
FIGS. 17A-17B illustrate orthogonal views of the anchor, in accordance with embodiments of the present disclosure.
Figure 17A:
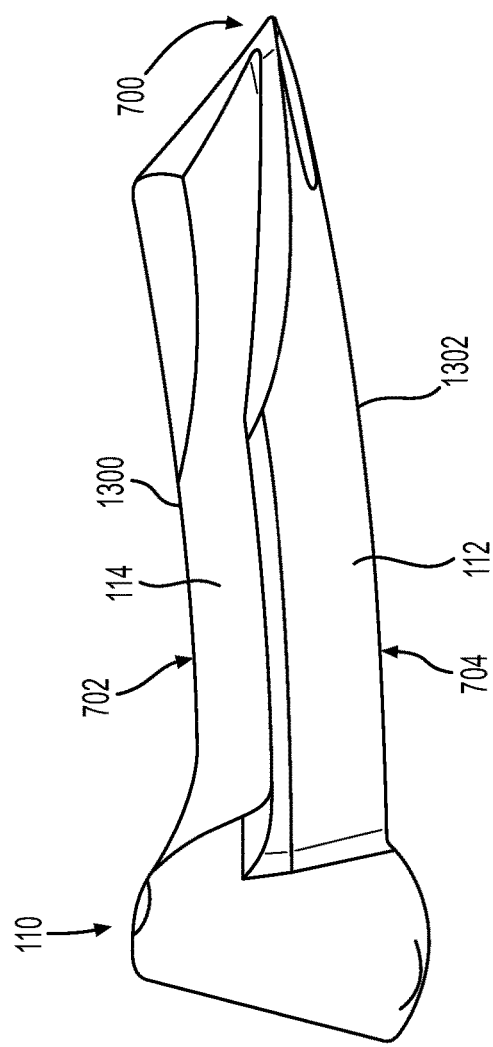

FIGS. 17A-17B illustrate orthogonal views of the anchor 104, in accordance with embodiments of the present disclosure. As illustrated in FIG. 17A, the anchor 104 includes the head portion 110 with the elongate shank 112 extending from the head portion 110. Further, the elongate fin 114 extends from the head portion 110 and along the surface 1500 of the elongate shank 112. As illustrated, the anchor 104 includes the concave side 702 of the anchor 104 formed along the outer top surface 1300 the elongate fin 114 and the convex side 704 formed along the outer bottom surface 1302 of the elongate shank 112. Further, the tip portion 700 of the anchor 104 is positioned on the convex side 704 of the anchor 104 at the end of the elongate shank 112. Referring to FIG. 17B, the tip portion 700 may be tapered such that the tip portion 700 of the anchor 104 becomes tangent to multiple areas of the spacer 102 (shown in FIG. 1) to ease insertion and ensure the proper trajectory of the anchor 104 into a corresponding vertebral body.

Figure 18:
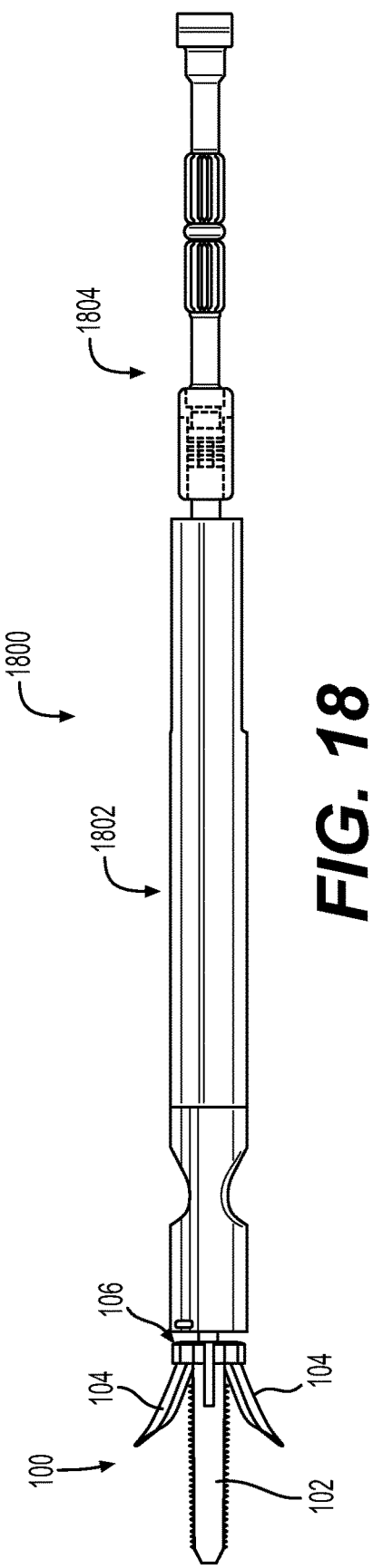
FIG. 18 illustrates a side view of a surgical implant system, in accordance with embodiments of the present disclosure.

FIG. 18 illustrates a side view of a surgical implant system 1800, in accordance with embodiments of the present disclosure. The surgical implant system 1800 includes the surgical implant 100 having the spacer 102 and the plurality of anchors 104. The anchors 104 configured for insertion through the eyelet 106 of the spacer 102 and into the vertical body to fasten the surgical implant 100 to the spine of a patient. Further, the surgical implant system 1800 includes an insertion device 1802 configured to align the anchor 104 with the spacer 102 and guide the anchor 104 through the eyelet 106 of the spacer 102 during insertion. Moreover, the surgical implant system 1800 includes an impactor 1804 1804 of the surgical implant system 1800 may be configured to drive the anchor 104 during insertion.

Figure 19:
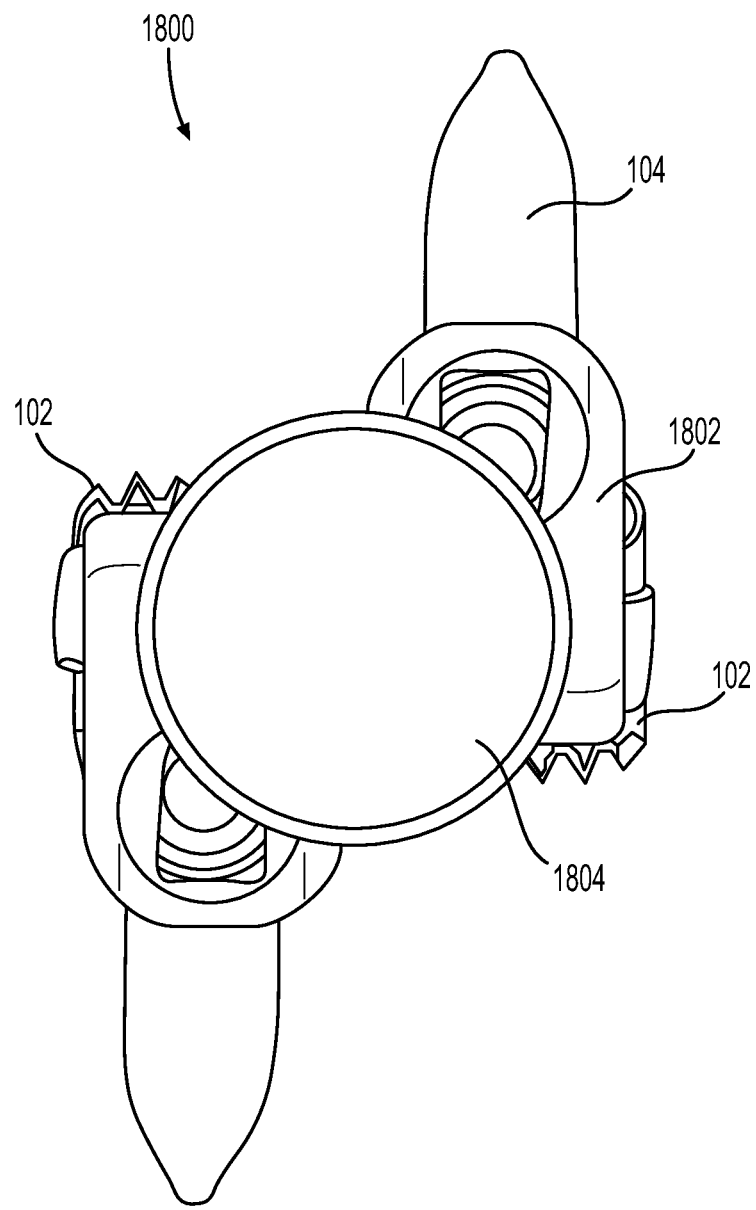
FIG. 19 illustrates a rear view of the surgical implant system, in accordance with embodiments of the present disclosure.

FIG. 19 illustrates a rear view of the surgical implant system 1800, in accordance with embodiments of the present disclosure. The insertion device 1802 and/or the impactor 1804 may be configured to permit visualization of the anchor 104 and/or the spacer 102 during insertion of the anchor 104 into a corresponding vertebral body. Further, the profile of the insertion device 1802 may provide desirable access to the disc space positioned between adjacent vertebral bodies via a lateral approach.

Figure 20:
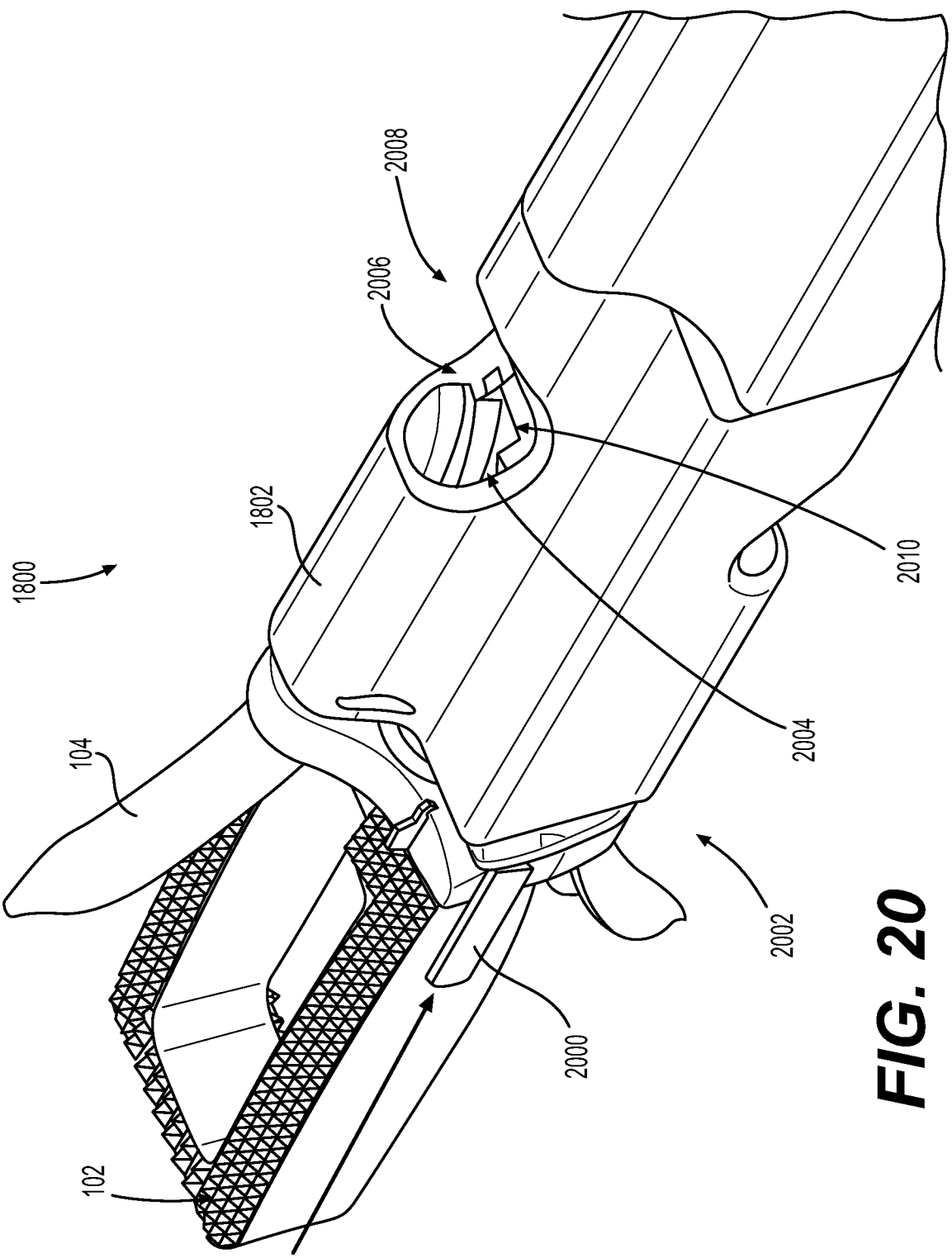
FIG. 20 illustrates a perspective view of the surgical implant system having the insertion device, in accordance with embodiments of the present disclosure.

FIG. 20 illustrates a perspective view of the surgical implant system 1800 having the insertion device 1802, in accordance with embodiments of the present disclosure. The insertion device 1802 may be configured to insert the spacer 102 into a space between adjacent vertebral bodies. The insertion device 1802 may include an insertion clamp 2000 (e.g., forked feature) disposed at a front portion 2002 of the insertion device 1802. The spacer 102 may be temporarily mounted to the insertion clamp 2000. The insertion clamp 2000 may be configured to detach from the spacer 102 after insertion of the spacer 102 into the space between the adjacent vertebral bodies.

Further, the insertion device 1802 may include at least one anchor loading chamber 2004 configured to receive and guide the anchor 104 through a corresponding eyelet 106 of the spacer 102 and into the vertebral body to secure the spacer 102 between adjacent vertebral bodies. The anchor 104 may be loaded into the anchor loading chamber 2004 prior to insertion of the spacer 102. Following insertion of the spacer 102, the anchor 104 may be driven through the anchor loading chamber 2004 for insertion through the eyelet 106 of the spacer 102 and into the vertebral body. As illustrated, the anchor loading chamber 2004 of the insertion device 1802 may include a curved key feature guide 2006 extending along a trajectory of the anchor loading chamber 2004. As set forth above, the head portion 110 of the anchor 104 comprises key cut features 1200 (shown in FIG. 12) configured to interface with the insertion device 1802 to restrain rotation, as well vertical and horizontal motion of the anchor 104 during insertion. Specifically, the key cut features 1200 are configured to interface with the curved key feature guide 2006.

The insertion device 1802 may further include a bowled anchor loading feature 2008 configured to provide ease of insertion with a gloved finger. The bowled anchor 104 feature may include a bowl-shaped cutout in the profile of the insertion device 1802 proximate an intake 2010 of the anchor loading chamber 2004.

Figure 21:
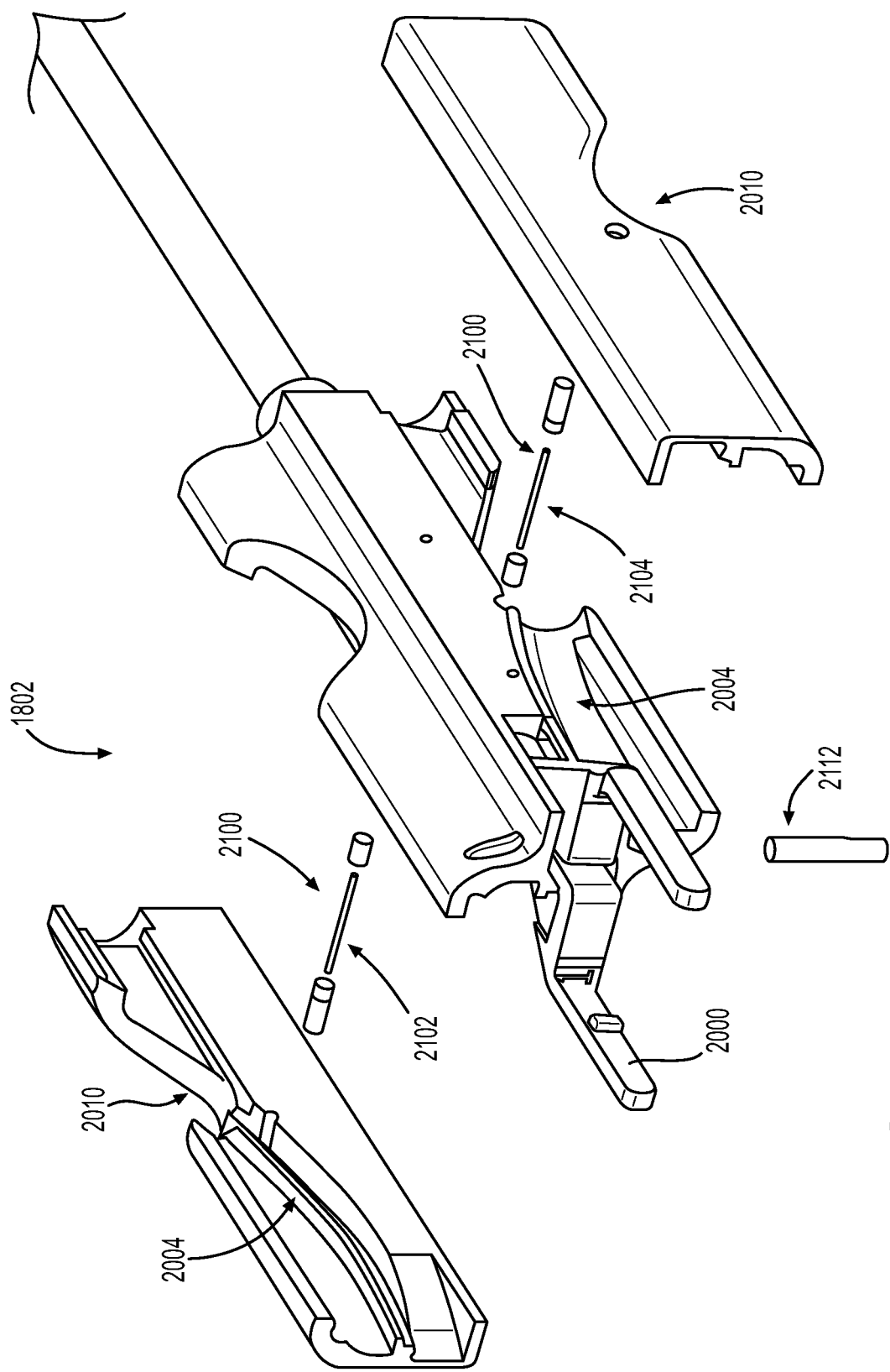
FIG. 21 illustrates an exploded view of the insertion device, in accordance with embodiments of the present disclosure.

FIG. 21 illustrates an exploded view of the insertion device 1802, in accordance with embodiments of the present disclosure. In the illustrated embodiment, the insertion device 1802 includes a plurality of spring wires 2100 (e.g., a first spring wire 2102 and second spring wire 2104) disposed proximate respective intakes 2010 of the corresponding anchor loading anchor loading chamber 2004s 2004 (e.g., a first anchor loading anchor loading chamber 2004 2106 and a second anchor loading anchor loading chamber 2004 2108). The respective spring wires 2100 may be configured to hold the anchors 104 in position within the insertion device 1802 prior to insertion of the anchors 104.

Further, the insertion device 1802 includes the insertion clamp 2000 configured to grip the spacer 102 device (shown in FIG. 20) during insertion of the spacer 102. As set forth above, the insertion clamp 2000 is configured to release the spacer 102 after insertion of the spacer 102 into the space between the adjacent vertebral bodies. In the illustrated embodiment, the insertion clamp 2000 may include a plurality of swept channels 2110 configured to allow anchors 104 to pass by the insertion clamp 2000 and proceed through the respective eyelets 106 of the spacer 102. Further, the insertion device 1802 may also include a pin mechanism 2112 configured to actively open the insertion clamp 2000. Moreover, the insertion device 1802 includes a cam and follower mechanism configured to actively close the insertion clamp 2000 to rigidly grip the spacer 102.

FIG. 22 illustrates a cross-sectional view of the surgical implant system 1800 with the anchor 104 loading into the anchor loading chamber 2004 of the insertion device 1802, in accordance with embodiments of the present disclosure. As illustrated, the tip portion 700 of the anchor 104 is aligned with and positioned proximate the intake 2010 of the anchor loading chamber 2004. The anchor 104 may be loaded into the anchor loading chamber 2004 by pressing on the anchor 104 (e.g., the head portion 110) with a finger. The bowled anchor loading feature 2008 may provide sufficient space to permit the finger to fully load the anchor 104 into the anchor loading chamber 2004.

FIG. 23 illustrates a cross-sectional view of the surgical implant system 1800 with the anchor 104 loaded in the anchor loading chamber 2004 of the insertion device 1802, in accordance with embodiments of the present disclosure. As illustrated, the anchor 104 is positioned within the anchor loading chamber 2004, and the spring wire 2100 of the insertion device 1802 is restraining the anchor 104 from moving along the guide path of the anchor loading chamber 2004. In particular, the spring wire 2100, extending across the anchor loading chamber 2004, is positioned within the hole feature 1104 of the anchor 104. Contact at the interface between the hole feature 1104 and the spring wire 2100 provides temporary containment of anchor 104 within the insertion device 1802.

Figure 24:
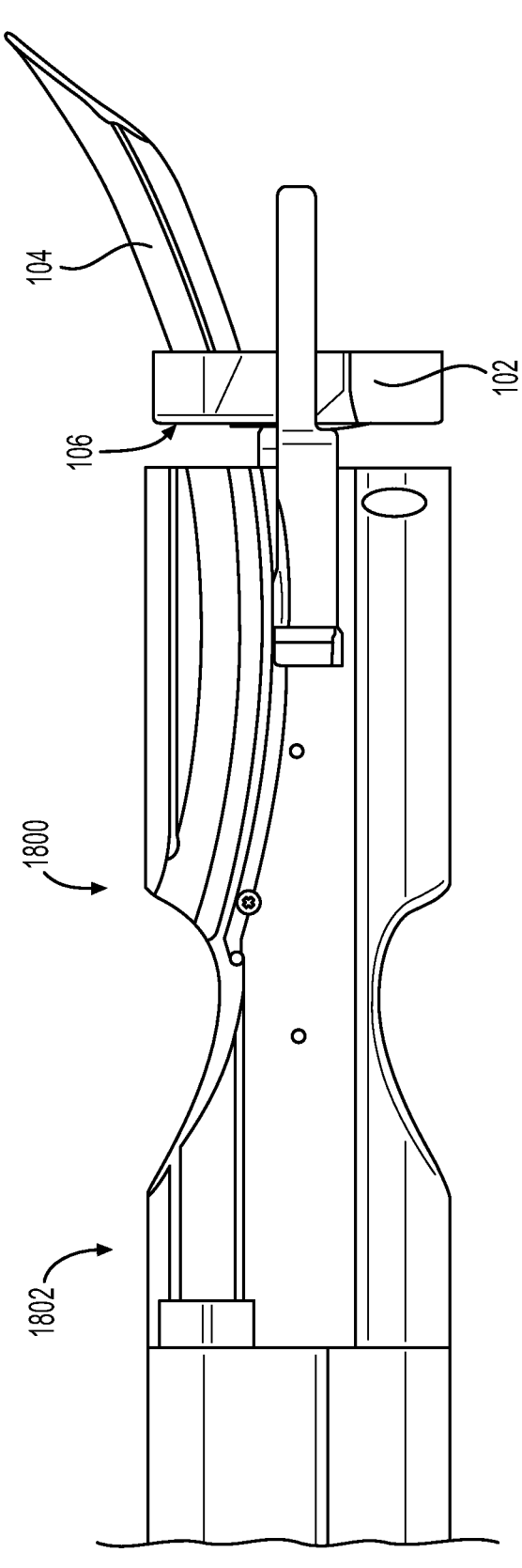
FIG. 24 illustrates a cross-sectional view of the surgical implant system with the anchor inserted through the eyelet of the spacer via the insertion device, in accordance with embodiments of the present disclosure.

FIG. 24 illustrates a cross-sectional view of the surgical implant system 1800 with the anchor 104 inserted through the eyelet 106 of the spacer 102 via the insertion device 1802, in accordance with embodiments of the present disclosure. As illustrated, the anchor 104 is in a fully inserted position.

Figure 25:
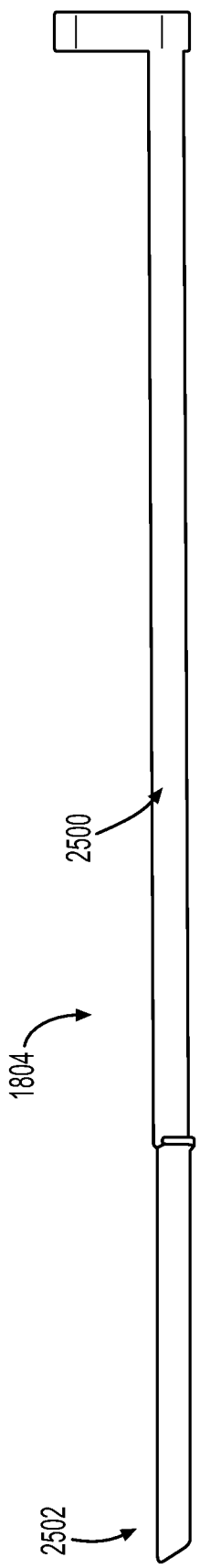
FIG. 25 illustrates a side view of an impactor, in accordance with embodiments of the present disclosure.

FIG. 25 illustrates a side view of an impactor 1804, in accordance with embodiments of the present disclosure. In some embodiments, the impactor 1804 has a cut-out feature 2500. The cut-out feature 2500 may be configured to make the impactor 1804 in line with a space for streamlined access to the anchor loading chamber 2004. The impactor 1804 may have a tip 2502 configured to contact the head portion 110 of the anchor 104 via the streamlined access and drive the anchor 104 via exerting forces on the head portion 110 of the anchor 104. Further, the tip 2502 of the impactor 1804 may have be angled tip 2502 (e.g., thirty-degree tip) configured to control vertical motion of the anchor 104.

Figure 26:
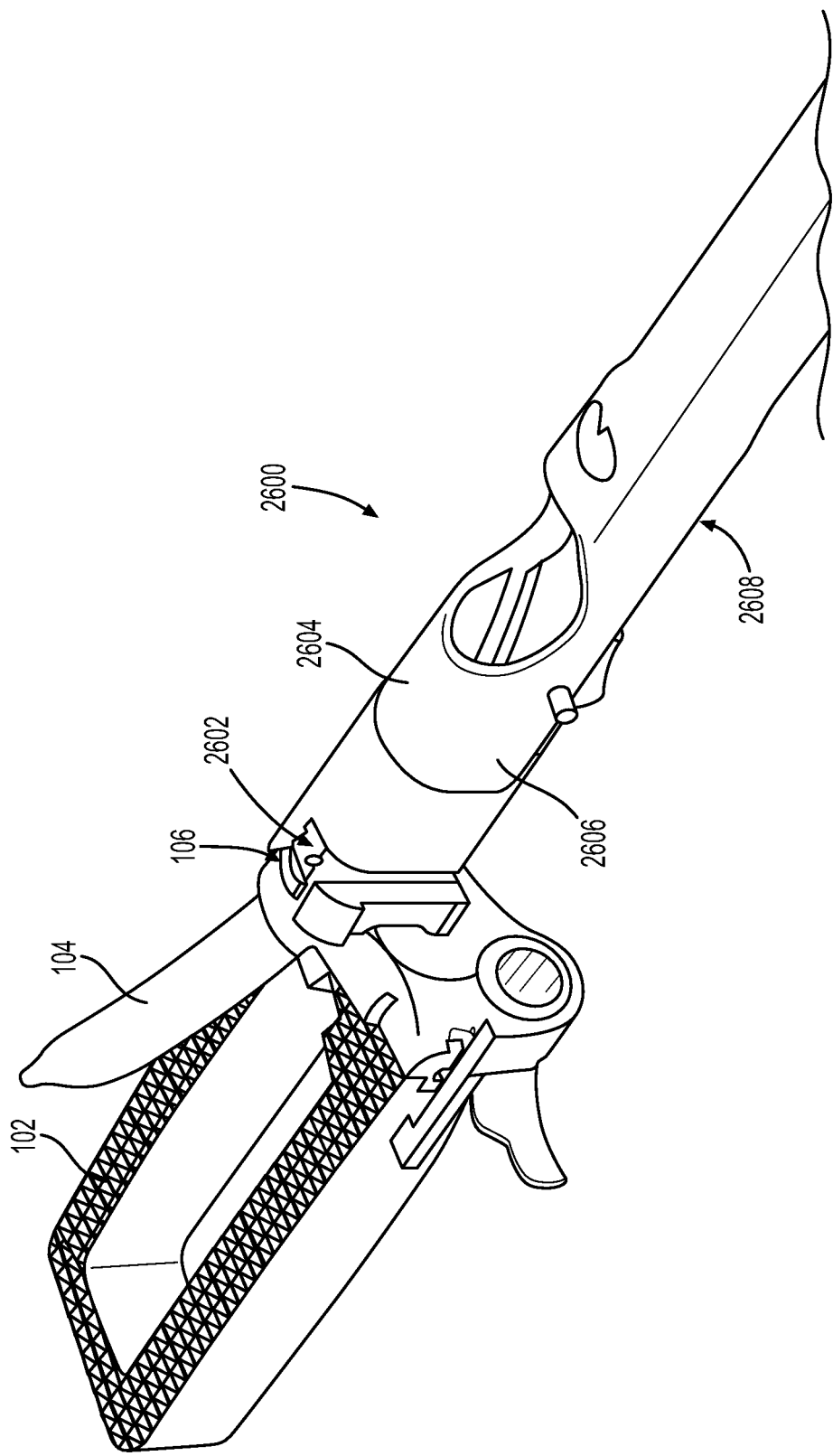
FIG. 26 illustrates a perspective view of a single anchor insertion device, in accordance with embodiments of the present disclosure.

FIG. 26 illustrates a perspective view of a single anchor insertion device 2600, in accordance with embodiments of the present disclosure. The single anchor insertion device 2600 may be configured to guide insertion of a single anchor 104 through a respective eyelet 106 of a corresponding spacer 102 (e.g., individual anchor insertion). In the illustrated embodiment, the single anchor insertion device 2600 includes a window 2602 for visualization of the anchor 104 and the spacer 102 during insertion. The window 2602 may be formed in a top surface 2604 of the single anchor insertion device 2600. However, in some embodiments, the window may be formed in a lateral surface 2606 or bottom surface 2608 of the single anchor insertion device 2600.

Figure 27:
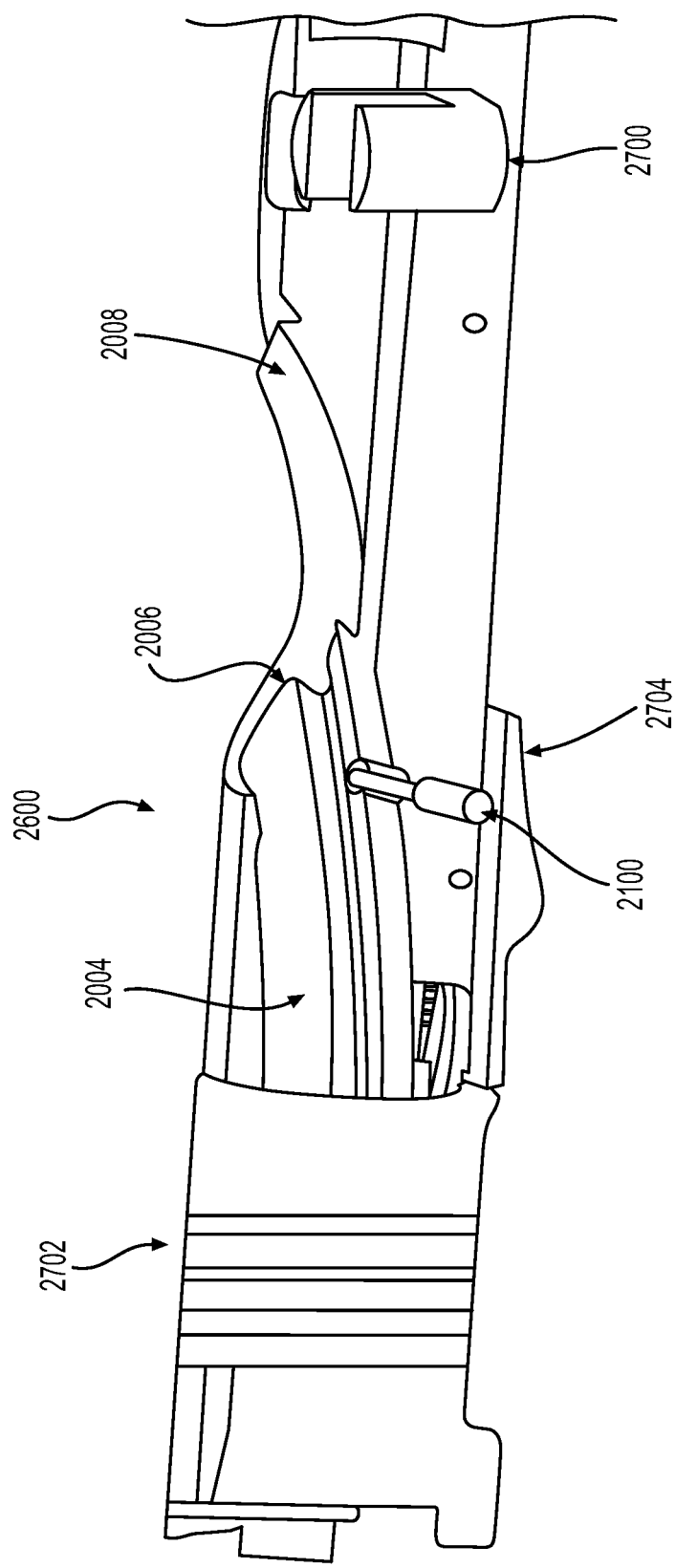
FIG. 27 illustrates a perspective sectional view of the single anchor insertion device, in accordance with embodiments of the present disclosure.

FIG. 27 illustrates a perspective sectional view of the single anchor insertion device 2600, in accordance with embodiments of the present disclosure. The single anchor insertion device 2600 may include the anchor loading chamber 2004 configured to receive and guide the anchor 104. To help guide the anchor 104, the single anchor insertion device 2600 may include the curved key feature guides 2006 configured to restrain rotational, vertical, and horizontal motion as the anchor 104 moves through the anchor loading chamber 2004. The single anchor insertion device 2600 may further include the bowled anchor loading feature 2008 configured to provide sufficient space for loading the anchor 104 into the anchor loading chamber 2004 with a finger. After loading the anchor 104 into the anchor loading chamber 2004, the single anchor insertion device 2600 includes the spring wire 2100 configured to interface with the hole feature 1104 of the anchor 104 to hold the anchor 104 in position within the anchor loading chamber 2004 prior to insertion of the anchor 104. The single anchor insertion device 2600 may further include a bushing 2700 configured to provide resistance to the impactor 1804 to control anchor insertion.

Moreover, the single anchor insertion device 2600 may include modular interchangeable tips 2702 to fit multiple spacer profiles. A spring-activated slider mechanism 2704 of the single anchor insertion device 2600 may be configured to hold the modular tip 2702 securely during insertion of the anchor 104 and reliably allows disconnection of the modular tip 2702 afterward insertion. Having modular tips 2702 may allow the single anchor insertion device 2600 to interface with multiple types of spacers 102 such that the single anchor insertion device 2600 may be universally used as an insertion device 1802 for spinal implant surgery based at least in part on availability of suitable modular tips 2702.

Figure 28:
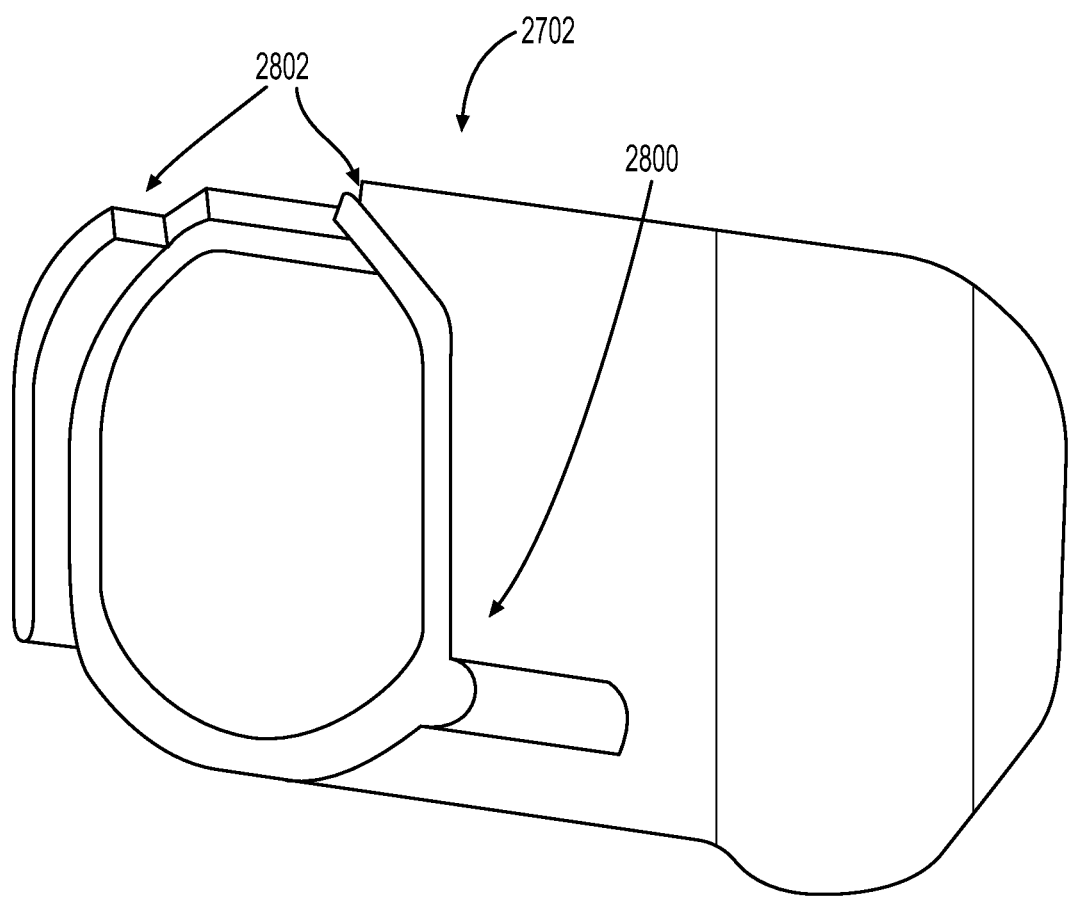
FIG. 28 illustrates a perspective view of a modular tip for the single anchor insertion device, in accordance with embodiments of the present disclosure.

FIG. 28 illustrates a perspective view of a modular tip 2702 for the single anchor insertion device 2600, in accordance with embodiments of the present disclosure. Each modular tip 2702 may have unique pin 2800 and wall features 2802 configured to fit corresponding spacer profiles. The pin 2800 and wall features 2802 may be configured to restrain movement of the insertion device 1802 with respect to the spacer 102 during insertion of the anchor 104.

Figure 29:
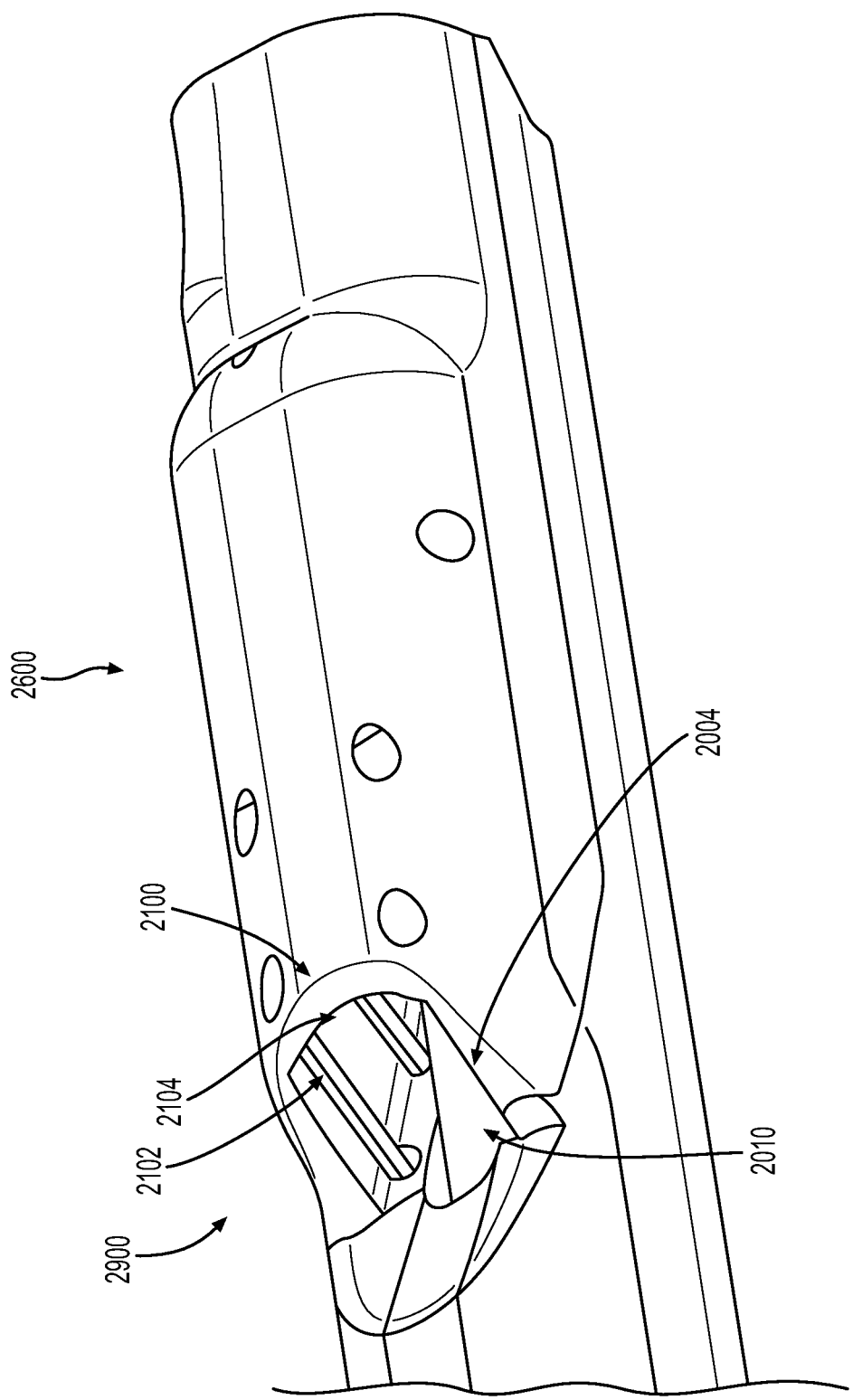
FIG. 29 illustrates a perspective view of an anchor retention mechanism for the single anchor insertion device, in accordance with embodiments of the present disclosure.

FIG. 29 illustrates a perspective view of an anchor retention mechanism 2900 for the single anchor insertion device 2600, in accordance with embodiments of the present disclosure. The anchor retention mechanism 2900 is configured to retain the anchor 104 within the insertion device 2600 until the anchor 104 is driven (e.g., ejected) via the impactor 1804. In the illustrated embodiment, the anchor retention mechanism 2900 includes the plurality of spring wires 2100 (e.g., a first spring wire 2102 and a second spring wire 2104) disposed within the anchor loading chamber 2004 proximate the intake 2010. The first and second spring wires 2102, 2104 may be disposed on opposing sides of the anchor loading chamber 2004. The head portion 110 of the anchor 104 is configured to rest in between the spring wires 2100 when loaded into the anchor loading chamber 2004. The spring wires 2100 (e.g., nitinol wires) are configured to function as springs that hold the head portion 110 in place until a force (e.g., from the impactor 1804) pushes the anchor 104 forward. As the anchor 104 is driven forward, the spring wires 2100 may bend out of the way to allow the head portion 110 to pass. The spring wires 2100 are configured to return to resting position for future use after the head portion 110 passes through the spring wires 2100.

Figure 30:
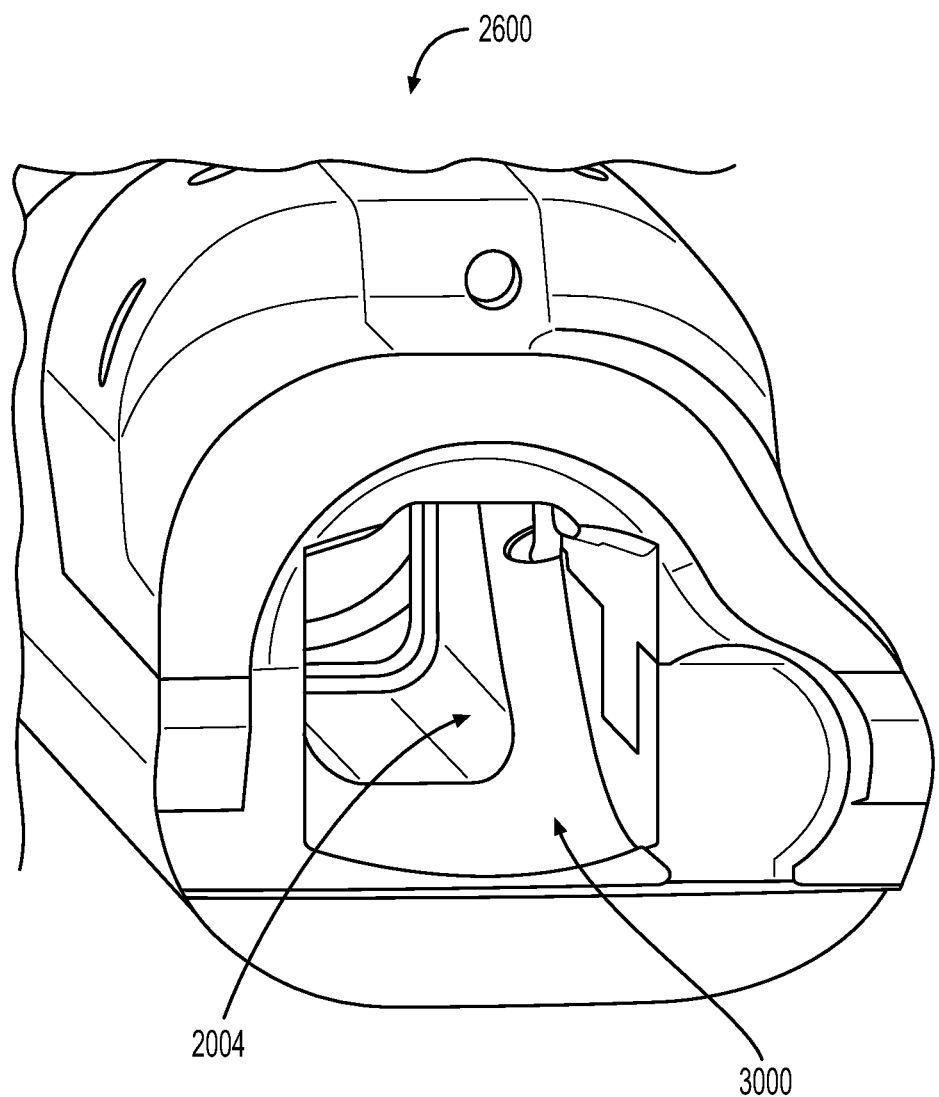
FIG. 30 illustrates a perspective view of the single anchor insertion device, in accordance with embodiments of the present disclosure.

FIG. 30 illustrates a perspective view of the single anchor insertion device 2600, in accordance with embodiments of the present disclosure. In the illustrated embodiment, an anchor channel 3000 (e.g., guide path) of the anchor loading chamber 2004 is configured to guide the anchor 104 through the anchor loading chamber 2004. As the anchor 104 is driven through the anchor loading chamber 2004 toward the spacer 102, the anchor 104 follows a trajectory of the anchor channel 3000.

Figure 31:
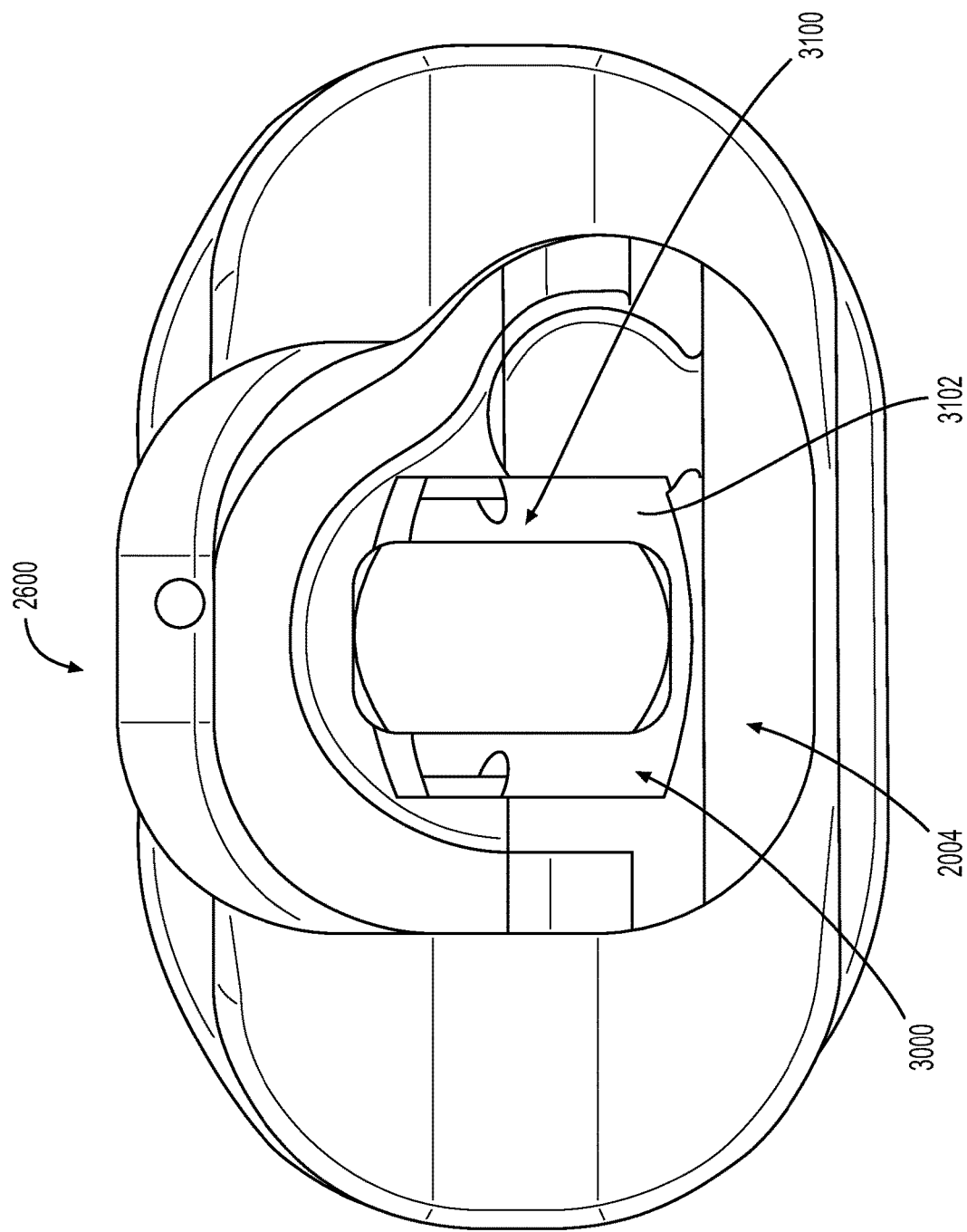
FIG. 31 illustrates a perspective view of an impactor channel of the single anchor insertion device, in accordance with embodiments of the present disclosure.

FIG. 31 illustrates a perspective view of an impactor channel 3100 of the single anchor insertion device 2600, in accordance with embodiments of the present disclosure. In the illustrated embodiment, the impactor channel 3100 is visible through the anchor loading chamber 2004. Indeed, the impactor channel 3100 connects to the anchor loading chamber 2004 through a bottom surface 3102 of the anchor channel 3000. During insertion of the anchor 104, the impactor 1804 is moved through the impactor channel 3100 toward the anchor channel 3000. Further, during insertion, the impactor 1804 is configured to protrude from the impactor channel 3100 into the anchor channel 3000 to contact the anchor 104 and drive the anchor 104 in a direction toward the spacer 102.

Figure 32B:
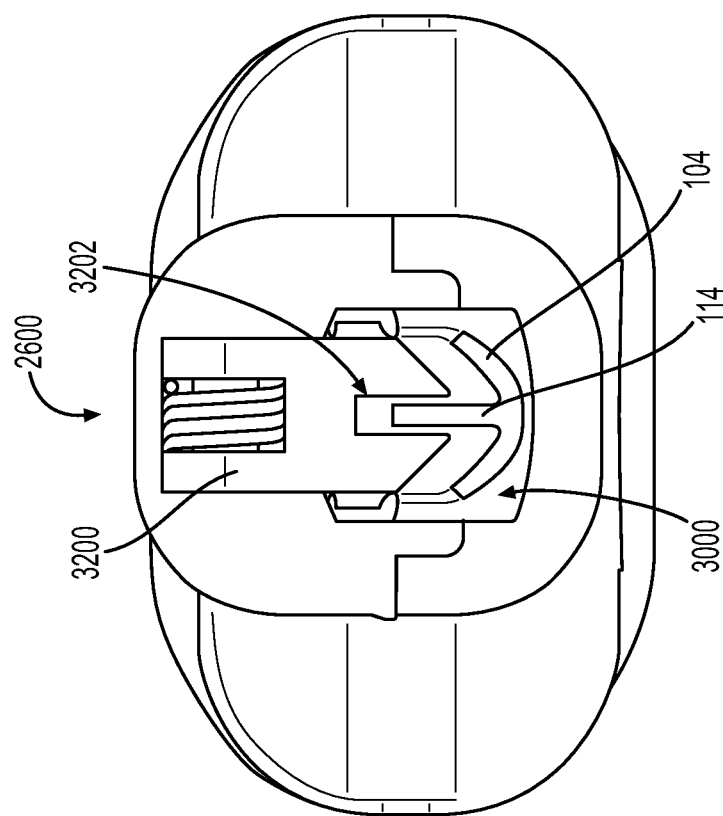
FIGS. 32A-32B illustrate cross-sectional views of the single anchor insertion device having a hinge feature, in accordance with embodiments of the present disclosure.
Figure 32A:
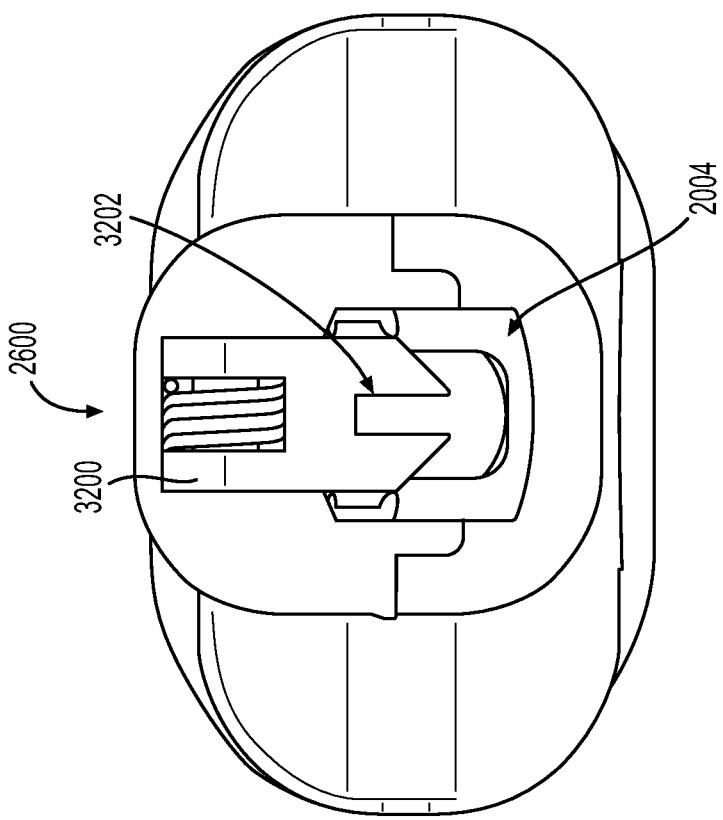

FIGS. 32A-32B illustrate cross-sectional views of the single anchor insertion device 2600 having a hinge feature 3200, in accordance with embodiments of the present disclosure. As illustrated in FIG. 32A, the hinge feature 3200 may be disposed within the anchor loading chamber 2004. Referring to FIG. 32B, the hinge feature 3200 may be configured to restrain rotation of the anchor 104 with respect to the single anchor insertion device 2600 as the anchor 104 passes through the anchor channel 3000. The hinge feature 3200 may include a slot 3202 configured to receive a portion of the elongate fin 114 of the anchor 104. That is, hinge feature 3200 may be positioned such that the elongate fin 114 is at least partially disposed within the slot 3202 of the hinge feature 3200 while the anchor 104 is positioned within and moving through the anchor channel 3000. Contact between the slot 3202 and the elongate fin 114 may restrain rotation of the anchor 104 with respect to the single anchor insertion device 2600.

FIG. 33 illustrates a cross-sectional view of the impactor 1804 entering the single anchor insertion device 2600, in accordance with embodiments of the present disclosure. In the illustrated embodiment, the anchor 104 is disposed within the anchor loading chamber 2004 with the head portion 110 retained by the spring wires 2100. Further, at least a portion of the elongate fin 114 is positioned within the slot 3202 of the hinge feature 3200.

Figure 34:
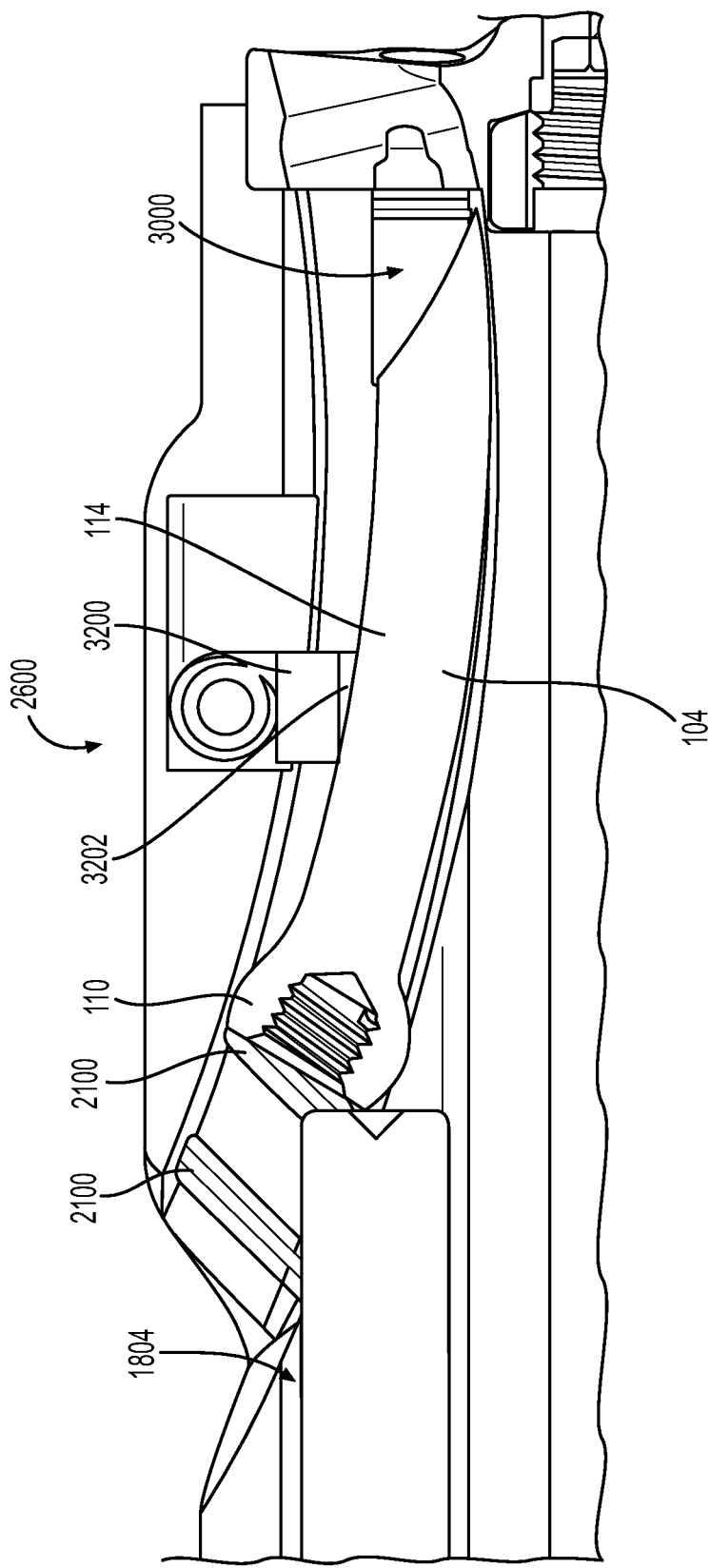
FIG. 34 illustrates a cross-sectional view of the impactor driving the anchor through the single anchor insertion device, in accordance with embodiments of the present disclosure.

FIG. 34 illustrates a cross-sectional view of the impactor 1804 driving the anchor 104 through the single anchor insertion device 2600, in accordance with embodiments of the present disclosure. In the illustrated embodiment, the impactor 1804 is in contact with the head portion 110 and driving the anchor 104 through the anchor channel 3000. Further, the impactor 1804 has driven the head portion 110 of the sufficiently forward such that the head portion 110 is no longer retained by the spring wires 2100. However, the elongate fin 114 is positioned within the slot 3202 of the hinge feature 3200 such that the hinge feature 3200 may restrain rotational movement of the anchor 104 with respect to the single anchor insertion device 2600.

Figure 35:
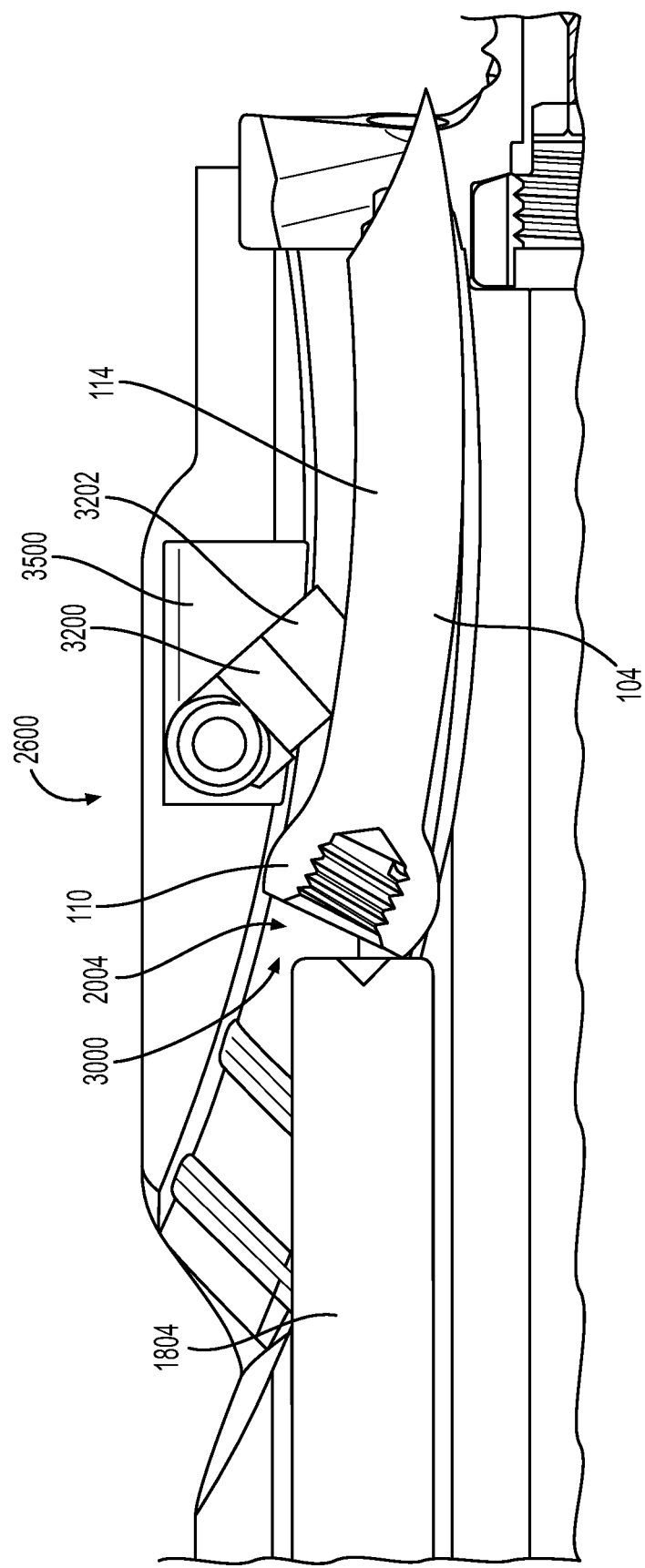
FIG. 35 illustrates a cross-sectional view of the hinge feature pivoting in response to the impactor driving the anchor through the single anchor insertion device, in accordance with embodiments of the present disclosure.

FIG. 35 illustrates a cross-sectional view of the hinge feature 3200 pivoting in response to the impactor 1804 driving the anchor 104 through the single anchor insertion device 2600, in accordance with embodiments of the present disclosure. As set forth above, the elongate fin 114 is positioned within the slot 3202 of the hinge feature 3200 such that the hinge feature 3200 may restrain rotational movement of the anchor 104 with respect to the single anchor insertion device 2600. However, the head portion 110 and/or other portions of the anchor 104 may not fit within the slot 3202 of the hinge feature 3200. Further, portions of the hinge feature 3200 proximate the slot 3202 may impede passage of the anchor 104 through the anchor channel 3000. The hinge feature 3200 may be configured to rotate within the anchor loading chamber 2004 to permit the head portion 110 and/or the other portions of the anchor 104 to pass through the anchor channel 3000. As illustrated, the single anchor insertion device 2600 may include a hinge recess 3500 configured to receive the hinge feature 3200 when the hinge feature 3200 rotates to permit passage of the anchor 104 through the anchor channel 3000.

Figure 36:
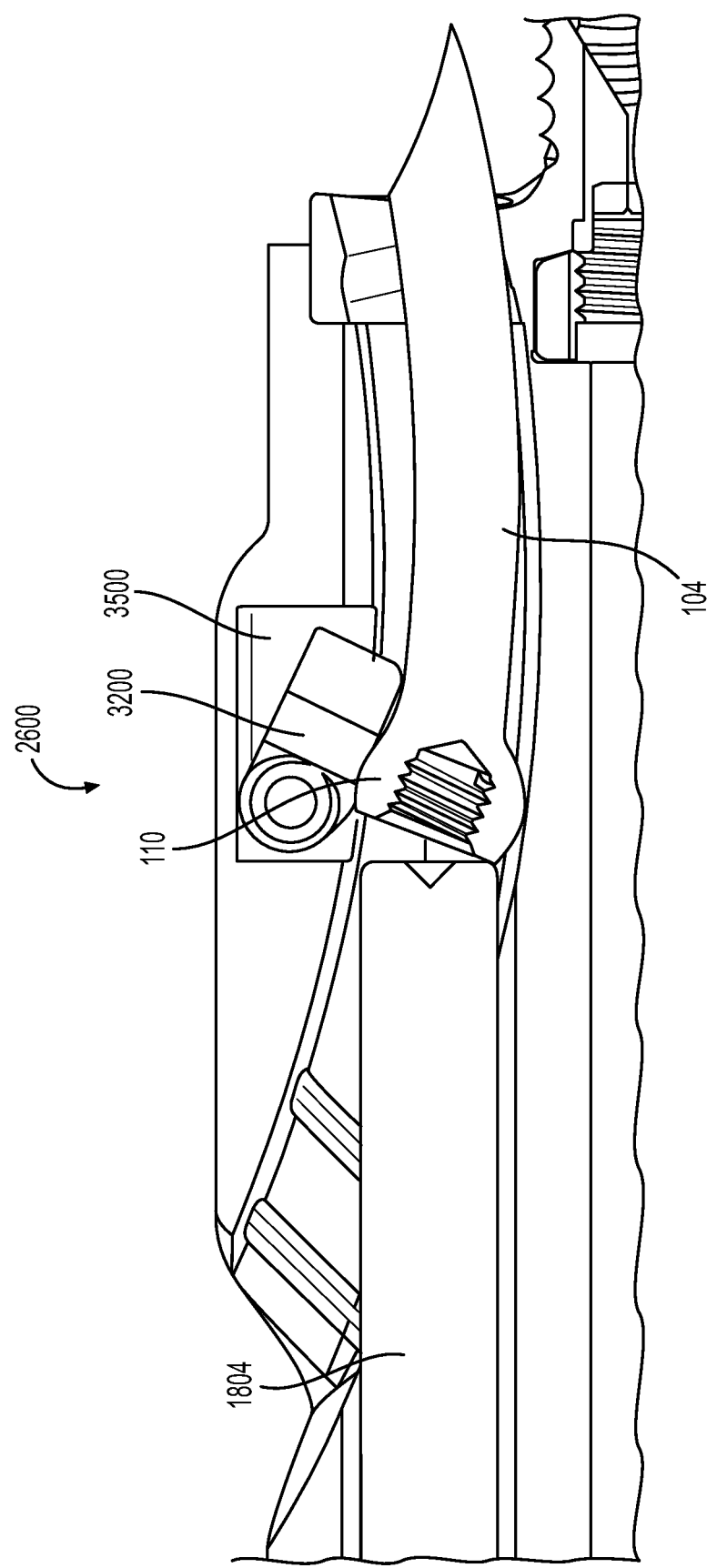
FIG. 36 illustrates a cross-sectional view of the hinge feature pivoting in response to the impactor driving the anchor through the single anchor insertion device, in accordance with embodiments of the present disclosure.

FIG. 36 illustrates a cross-sectional view of the hinge feature 3200 pivoting in response to the impactor 1804 driving the anchor 104 through the single anchor insertion device 2600, in accordance with embodiments of the present disclosure. As illustrated, the hinge feature 3200 pivots further into the hinge recess 3500 in response to contact with the head portion 110 of the anchor 104.

Figure 37:
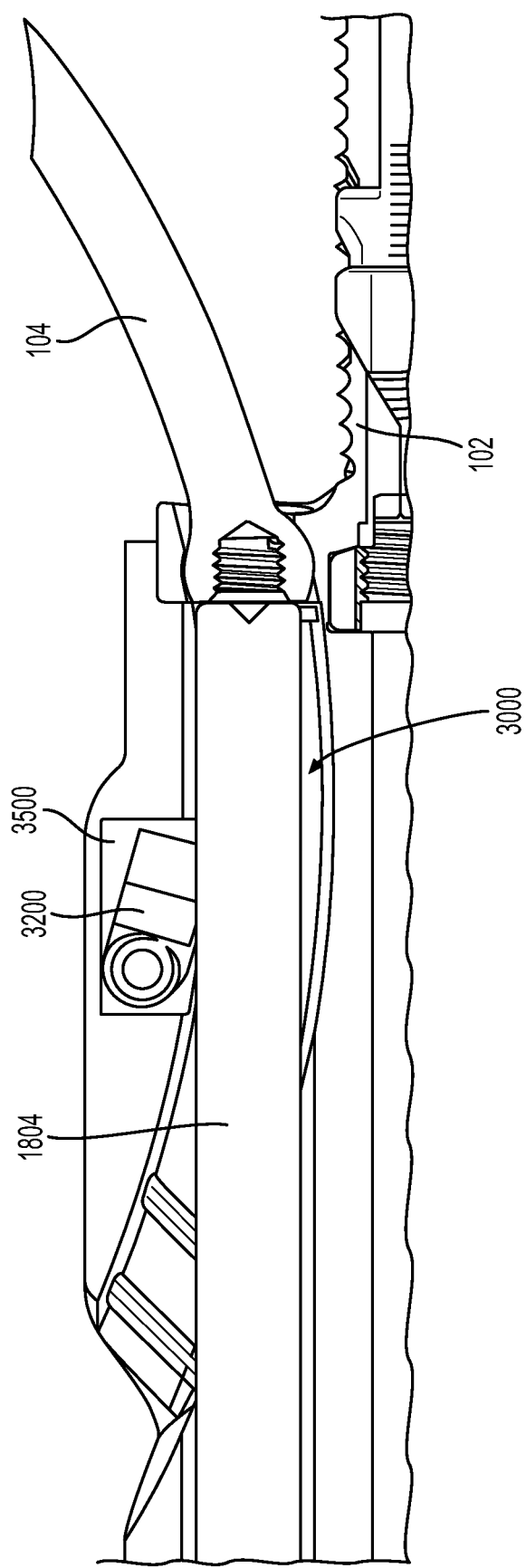
FIG. 37 illustrates a cross-sectional view of the impactor driving the anchor to a fully seated position in the spacer, in accordance with embodiments of the present disclosure.

FIG. 37 illustrates a cross-sectional view of the impactor 1804 driving the anchor 104 to a fully seated position in the spacer 102, in accordance with embodiments of the present disclosure. As illustrated, the impactor 1804 is disposed within the anchor channel 3000 to drive the anchor 104. Contact between the impactor 1804 and the hinge feature 3200 maintains the position of the hinge feature 3200 within the hinge recess 3500.

Figure 38:
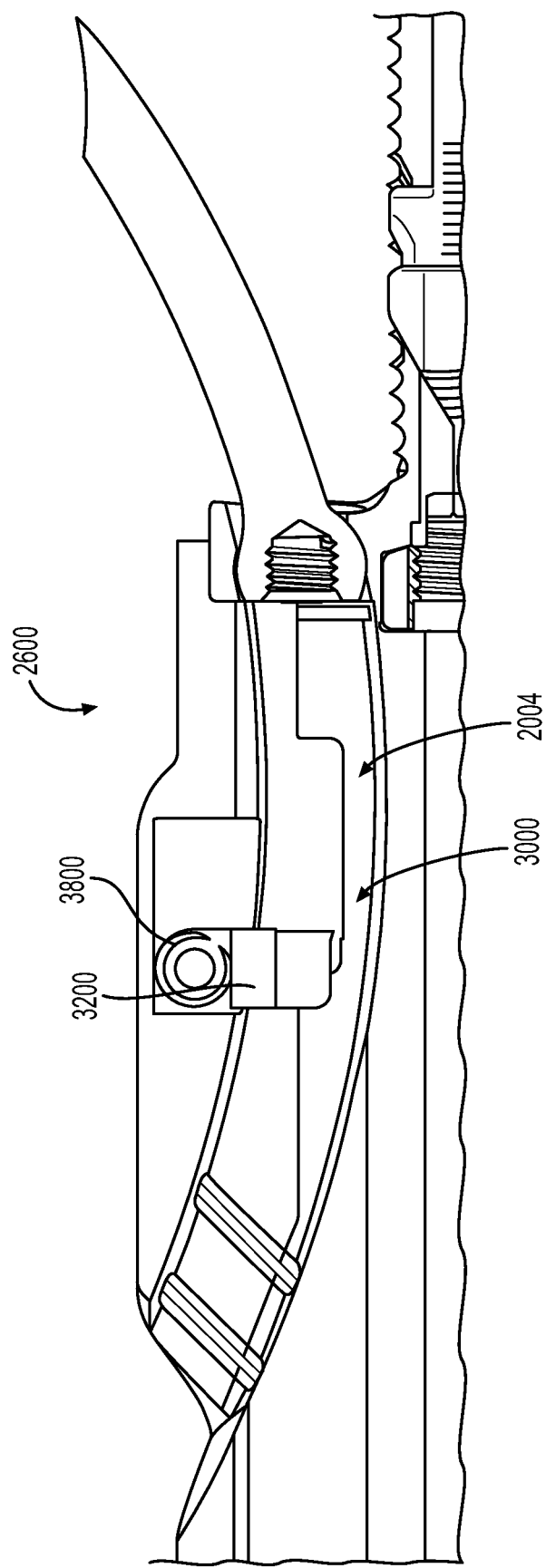
FIG. 38 illustrates a cross-sectional view of the hinge feature rotated into the anchor loading chamber of the single anchor insertion device in response to removal of the impactor, in accordance with embodiments of the present disclosure.

FIG. 38 illustrates a cross-sectional view of the hinge feature 3200 rotated into the anchor loading chamber 2004 of the single anchor insertion device 2600 in response to removal of the impactor 1804, in accordance with embodiments of the present disclosure. The hinge feature 3200 may include a spring feature 3800 configured to bias the hinge feature 3200 to rotate to a position within the anchor channel 3000. Thus, after insertion, the hinge feature 3200 is configured to move back into place within the anchor channel 3000 in response to removal of the impactor 1804.

Figure 39:
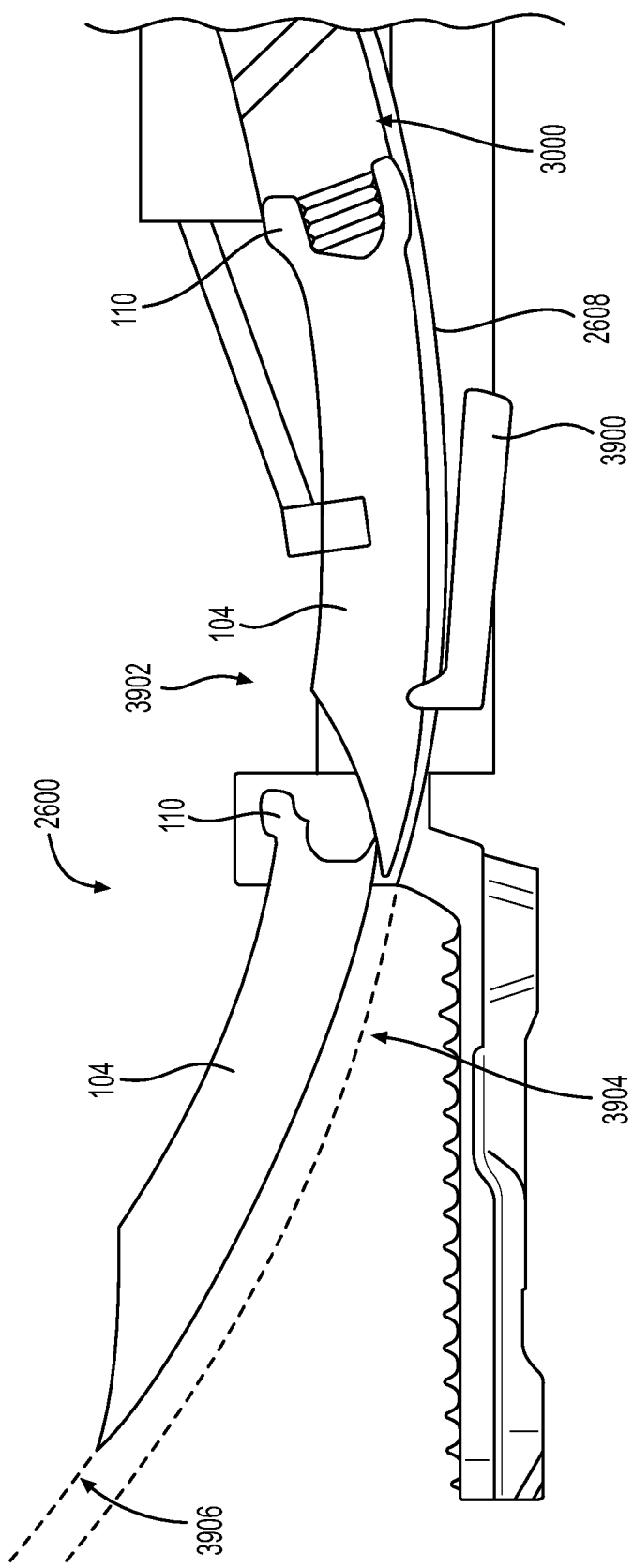
FIG. 39 illustrates a cross-sectional view of the single anchor insertion device having a spring mechanism, in accordance with embodiments of the present disclosure.

FIG. 39 illustrates a cross-sectional view of the single anchor insertion device 2600 having a spring mechanism 3900, in accordance with embodiments of the present disclosure. The single anchor insertion device 2600 may include the spring mechanism 3900 disposed proximate a bottom surface 2608 of the anchor channel 3000. In some embodiments, the spring mechanism 3900 may be positioned proximate an outlet 3902 of the anchor channel 3000. The spring mechanism 3900 may be configured to bias the anchor 104 to correct for differences between an insertion trajectory 3904 and desired final trajectory 3906 for the anchor 104. In some embodiments, the spring mechanism 3900 may include a metal spring tab. The spring mechanism 3900 may be positioned under the anchor 104 to lift the anchor 104 into a correct placement for insertion into the vertebral body. The spring mechanism 3900 may be flexible such that the spring mechanism 3900 may deform to permit passage of the head portion 110 of the anchor 104 and return to resting position for further usage in response to removal of contact with the head portion 110.

Figure 40:
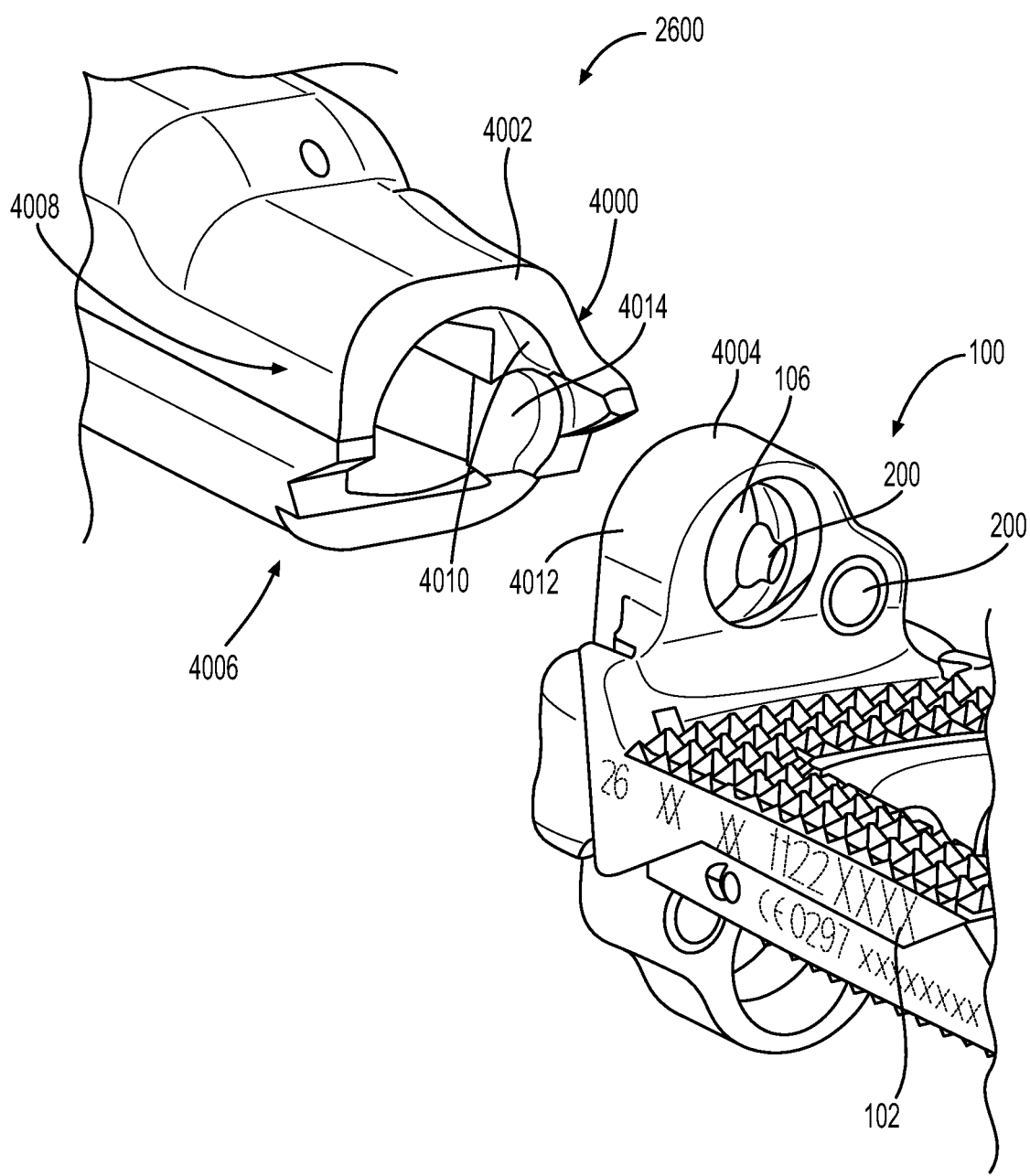
FIG. 40 illustrates a perspective view of the single anchor insertion device having an alignment mechanism, in accordance with embodiments of the present disclosure.

FIG. 40 illustrates a perspective view of the single anchor insertion device 2600 having an alignment mechanism 4000, in accordance with embodiments of the present disclosure. The alignment mechanism 4000 may be configured to interface with a portion of the surgical implant 100 to align the single anchor insertion device 2600 with respect to the at least one eyelet 106 of the spacer 102. In the illustrated embodiment, the alignment mechanism 4000 includes a rib feature 4002 configured to interface with a plate 4004 of the spacer 102, which houses the eyelet 106. The rib feature 4002 may protrude out from an outlet end 4006 of the single anchor insertion device 2600. In some embodiments, the rib feature 4002 may protrude out from a top portion 4008 of the outlet end 4006. The rib feature 4002 may be formed (e.g., shaped, sized) to fit around the plate that houses the eyelet 106 such that the rib feature 4002 may mesh with the plate 4004 during insertion. An inner surface 4010 of the rib feature 4002 may contact an outer surface 4012 of the plate 4004 in a meshed position. The interface between the rib feature 4002 and the plate 4004 in the meshed position may be configured to align the single anchor insertion device 2600 with respect to the eyelet 106 for insertion of the anchor 104, as well restrain movement of the single anchor insertion device 2600 with respect to the spacer 102. Moreover, the single anchor insertion device 2600 may also include a cutout feature 4014 in the outlet end 4006 of the single anchor insertion device 2600 to provide space for a blocking screw 200, such that the blocking screw 200 is not damaged during insertion.

Figure 41:
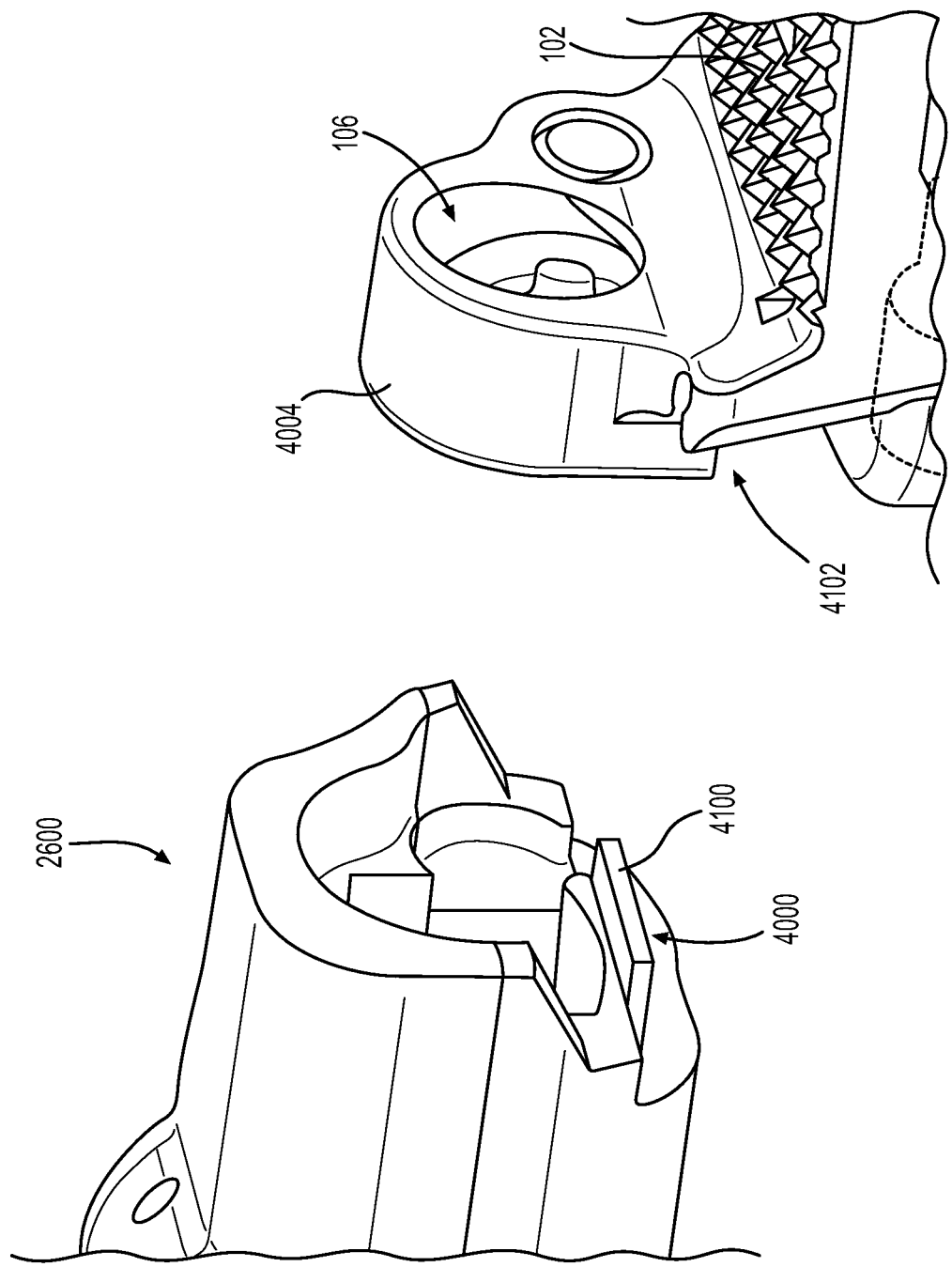
FIG. 41 illustrates a perspective view of the single anchor insertion device having another alignment mechanism, in accordance with embodiments of the present disclosure.

FIG. 41 illustrates a perspective view of the single anchor insertion device 2600 having another alignment mechanism 4000, in accordance with embodiments of the present disclosure. The alignment mechanism 4000 may include a tab 4100 configured to interface with the spacer 102 to align the single anchor insertion device 2600 with the eyelet 106 of the spacer 102 for insertion of the anchor 104. The tab 4100 for may provide support underneath implant eyelet 106. The tab 4100 may be configured for insertion into an open space 4102 positioned beneath the plate 4004 of the spacer 102 when the spacer 102 is in an expanded position. The tab 4100 may be a rigid protrusion. However, in some embodiments, the tab 4100 may be configured to retract into the single anchor insertion device 2600 when the spacer 102 is in a closed position so that the single anchor insertion device 2600 may interface with the spacer 102 in the closed position.

Figure 42:
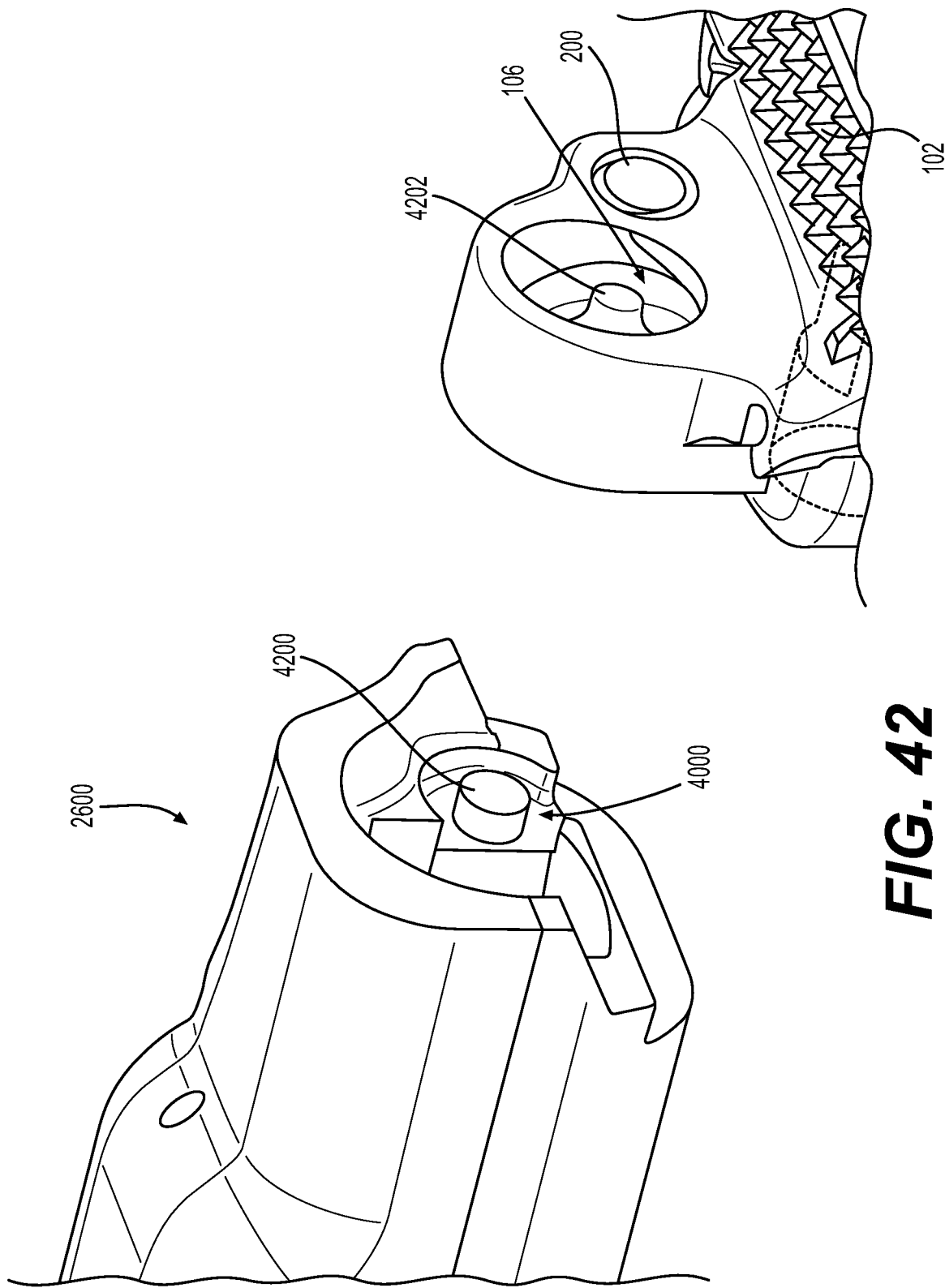
FIG. 42 illustrates a perspective view of the single anchor insertion device having another alignment mechanism, in accordance with embodiments of the present disclosure.

FIG. 42 illustrates a perspective view of the single anchor insertion device 2600 having another alignment mechanism 4000, in accordance with embodiments of the present disclosure. The alignment mechanism 4000 may include a peg 4200 configured to interface with a bore 4202 in the spacer 102 to align the single anchor insertion device 2600 with the eyelet 106 of the spacer 102 for insertion of the anchor 104. The peg 4200 may be configured to sit in the blocking screw 200 of the spacer 102. In some embodiments, the peg 4200 may be configured to inserted into the blocking screw 200 to provided support as well as align the single anchor insertion device 2600 with the eyelet 106 of the spacer 102.

Figure 43:
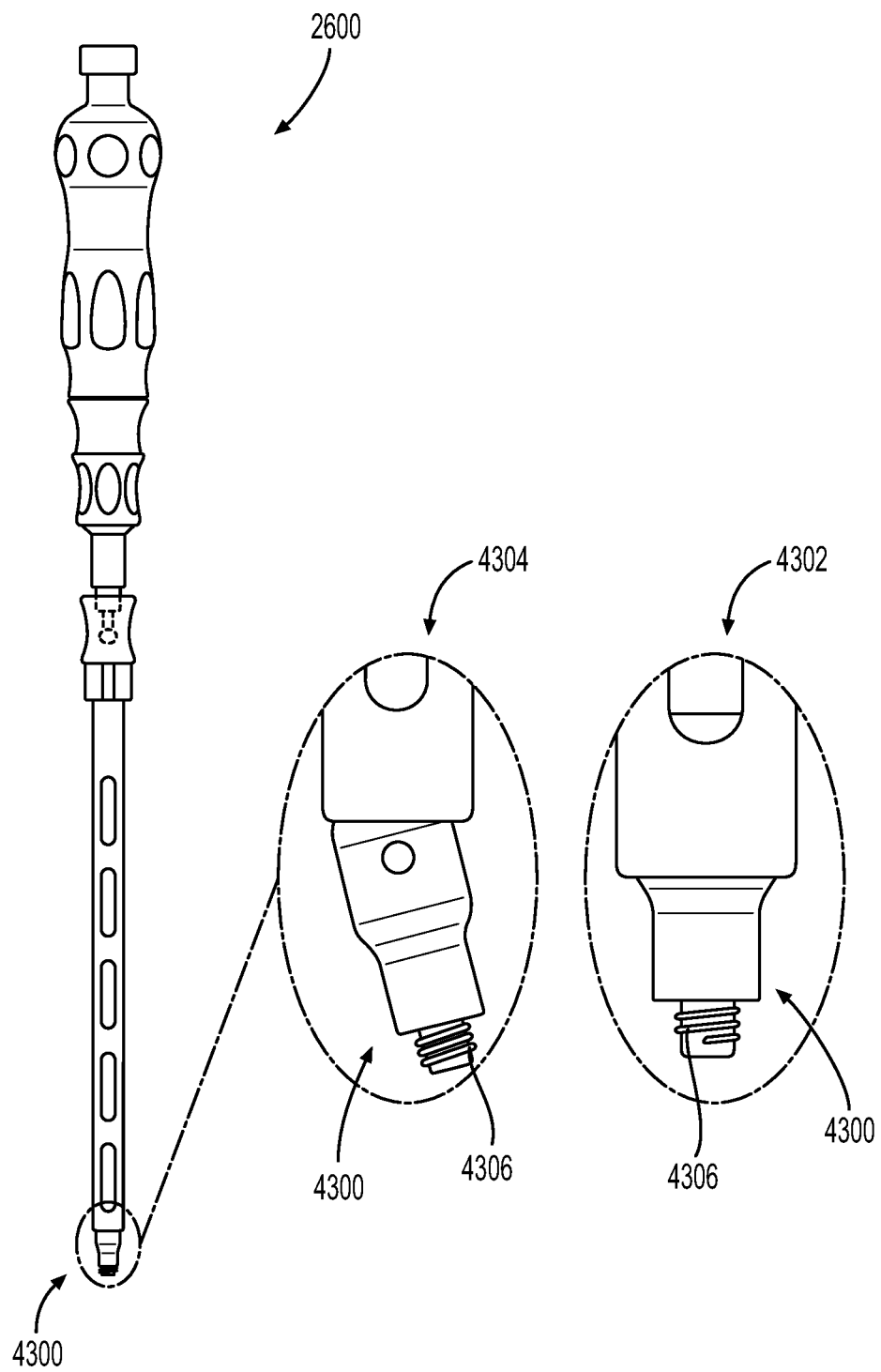
FIG. 43 illustrates a perspective view of the single anchor insertion device having a pivoting distal tip, in accordance with embodiments of the present disclosure.

FIG. 43 illustrates a perspective view of the single anchor insertion device 2600 having a pivoting distal tip 4300, in accordance with embodiments of the present disclosure. The pivoting distal tip 4300 may have a locked position 4302 and an unlocked position 4304. In the unlocked position, the pivoting distal tip 4300 may angulate up to fifteen degrees. In the locked position, the pivoting distal tip 4300 becomes rigid with respect to the single anchor insertion device 2600. The pivoting distal tip 4300 may include threading 4306. In some embodiments, the pivoting distal tip 4300 may be threaded into the head portion 110 of an anchor 104 for insertion or removal of the anchor 104.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Various advantages of the present disclosure have been described herein, but embodiments may provide some, all, or none of such advantages, or may provide other advantages.

What is claimed is:

1. A surgical implant system, comprising:
   a surgical implant for securing adjacent vertebrae of a spine to each other, wherein the surgical implant comprises a spacer having at least one implant eyelet; and
   at least one vertebral anchor configured for insertion through the at least one implant eyelet to fasten the surgical implant to the spine, the at least one vertebral anchor comprising:
   a head portion;
   an elongate shank extending from the head portion;
   an elongate fin extending from the head portion and along a surface of the elongate shank, the elongate shank and the elongate fin forming a generally t-shaped cross-section; and
   a tip portion,
   an insertion device configured to insert the at least one vertebral anchor through the at least one implant eyelet to fasten the surgical implant to the spine,
   wherein the insertion device comprises a hinge feature comprising a slot configured to interface with the elongate fin to restrain rotation of the at least one vertebral anchor with respect to the insertion device during insertion.

2. The surgical implant system of claim 1, further comprising a screw configured to configured for insertion through an additional implant eyelet of the surgical implant.

3. The surgical implant system of claim 1, wherein the surgical implant comprises a plurality of moveable actuators configured to move in response to mechanical input to expand the surgical implant.

4. The surgical implant system of claim 1, wherein the at least one vertebral anchor and a second vertebral anchor are configured for insertion at divergent orientations with respect to each other.

5. The surgical implant system of claim 1, wherein the elongate shank comprises a curved profile, wherein a trajectory of the curved profile is between five and fifteen degrees.

6. The surgical implant system of claim 1, wherein the elongate shank comprises a distal end positioned opposite a proximal end secured to the head portion, wherein the distal end is tapered to form the tip portion.

7. The surgical implant system of claim 1, wherein the elongate fin is tapered proximate the tip portion.

8. The surgical implant system of claim 1, wherein the elongate shank comprises a double beveled profile proximate a distal end of the elongate shank.

9. A surgical implant system, comprising:
   a surgical implant for securing adjacent vertebrae of a spine to each other, wherein the surgical implant comprises a spacer having at least one implant eyelet; and
   at least one vertebral anchor configured for insertion through the at least one implant eyelet to fasten the surgical implant to the spine, the at least one vertebral anchor comprising:
   a head portion comprising an angled face formed via a seventy-five to eighty-five degree flat cut into the head portion, the angled face configured to sit flush with the at least one implant eyelet after insertion;
   an elongate shank extending from the head portion; and
   an elongate fin extending from the head portion and along a surface of the elongate shank, the elongate shank and the elongate fin forming a generally t-shaped cross-section
   an insertion device configured to insert the at least one vertebral anchor through the at least one implant eyelet to fasten the surgical implant to the spine,
   wherein the insertion device comprises a wire retention mechanism configured to hold the at least one vertebral anchor in position within the insertion device prior to insertion.

10. The surgical implant system of claim 9, wherein the at least one vertebral anchor comprises a concave side formed along the elongate fin and a convex side formed along the elongate shank, wherein the tip portion is positioned at the convex side of the anchor, and wherein an end portion extends between a tip portion and a distal end of the concave side of the elongate fin.

11. The surgical implant system of claim 9, wherein the at least one vertebral anchor comprises a concave side formed along the elongate shank and a convex side formed along the elongate fin, and wherein a tip portion is positioned at the concave side of the anchor.

12. The surgical implant system of claim 9, wherein the head portion comprises a threaded counterbore extending into the angled face in a direction toward the elongate shank and the elongate fin.

13. The surgical implant system of claim 9, wherein a portion of the threaded counterbore proximate the angled face comprises a chamfer.

14. The surgical implant system of claim 9, wherein the elongate shank comprises sharpened serrations proximate a distal end of the elongate shank.

15. A surgical implant system, comprising:
    a surgical implant for securing adjacent vertebrae of a spine to each other, wherein the surgical implant comprises a spacer having at least one implant eyelet;
    at least one vertebral anchor configured for insertion through the at least one implant eyelet to fasten the surgical implant to the spine, the at least one vertebral anchor comprising:
    a head portion;
    an elongate shank extending from the head portion; and
    an elongate fin extending from the head portion and along a surface of the elongate shank, the elongate shank and the elongate fin forming a generally t-shaped cross-section; and
    an insertion device configured to insert the at least one vertebral anchor through the at least one implant eyelet to fasten the surgical implant to the spine
    wherein the insertion device comprises a wire retention mechanism configured to hold the at least one vertebral anchor in position within the insertion device prior to insertion.

16. The surgical implant system of claim 15, wherein the head portion comprises key cut features configured to interface with the insertion device to restrain rotation of the at least one vertebral anchor during insertion.

17. The surgical implant system of claim 15, wherein an anchor loading chamber of the insertion device comprises a curved key feature guide extending along a trajectory of the anchor loading chamber.

18. The surgical implant system of claim 15, wherein the insertion device comprises a hinge feature comprising a slot configured to interface with the elongate fin to restrain rotation of the at least one vertebral anchor with respect to the insertion device during insertion.

19. The surgical implant system of claim 15, wherein the insertion device comprises an alignment mechanism configured to interface with a portion of the surgical implant to align the insertion device with respect to the at least one implant eyelet for insertion of the anchor.

\* \* \* \* \*